United States Patent
Lim et al.

(10) Patent No.: US 9,458,489 B2
(45) Date of Patent: Oct. 4, 2016

(54) MICROFLUIDICS SORTER FOR CELL DETECTION AND ISOLATION

(75) Inventors: Chwee Teck Lim, Singapore (SG); Jongyoon Han, Cambridge, MA (US); Han Wei Hou, Singapore (SG); Ali Asgar Bhagat, Singapore (SG); Krystyn J. Van Vliet, Cambridge, MA (US); Wong Cheng Lee, Singapore (SG)

(73) Assignees: Massachusetts Institute of Technology, Cambridge, MA (US); National University of Singapore, Singapore (SG)

( * ) Notice: Subject to any disclaimer, the term of this patent is extended or adjusted under 35 U.S.C. 154(b) by 0 days.

(21) Appl. No.: 13/582,263

(22) PCT Filed: Mar. 4, 2011

(86) PCT No.: PCT/US2011/027276
§ 371 (c)(1),
(2), (4) Date: Dec. 10, 2012

(87) PCT Pub. No.: WO2011/109762
PCT Pub. Date: Sep. 9, 2011

(65) Prior Publication Data
US 2013/0130226 A1    May 23, 2013

Related U.S. Application Data

(60) Provisional application No. 61/310,387, filed on Mar. 4, 2010, provisional application No. 61/383,881, filed on Sep. 17, 2010.

(51) Int. Cl.
*G01N 33/574* (2006.01)
*C12Q 1/04* (2006.01)
*B01L 3/00* (2006.01)
*C12Q 1/02* (2006.01)
*G01N 15/14* (2006.01)

(52) U.S. Cl.
CPC ............ *C12Q 1/04* (2013.01); *B01L 3/50273* (2013.01); *B01L 3/502761* (2013.01); *C12Q 1/025* (2013.01); *B01L 2200/0636* (2013.01); *B01L 2300/0864* (2013.01); *B01L 2400/0457* (2013.01); *B01L 2400/086* (2013.01); *G01N 2015/149* (2013.01); *G01N 2015/1415* (2013.01)

(58) Field of Classification Search
CPC  B03D 1/1431; B03D 1/1456; B03D 1/1418; B03D 1/1412; B03D 1/1425; B03D 1/1475; B03D 1/1493; B01L 2400/0487; B01L 2200/668; B01L 2300/816; B01L 2300/681; B01L 2300/806; B01L 2300/1822; G01N 33/56972; G01N 15/0255; G01N 15/04; G01N 15/1485
See application file for complete search history.

(56) References Cited

U.S. PATENT DOCUMENTS

| | | | |
|---|---|---|---|
| 7,294,503 B2 | 11/2007 | Quake et al. | |
| 7,309,486 B1 | 12/2007 | Zamoyski | |
| 7,517,453 B2 | 4/2009 | Bitensky et al. | |
| 8,186,913 B2 | 5/2012 | Toner et al. | |
| 8,208,138 B2 | 6/2012 | Papautsky et al. | |
| 2007/0026381 A1 | 2/2007 | Huang et al. | |
| 2007/0131622 A1 | 6/2007 | Oakey et al. | |
| 2007/0264675 A1 | 11/2007 | Toner et al. | |
| 2009/0014360 A1* | 1/2009 | Toner et al. | 209/208 |
| 2009/0050538 A1 | 2/2009 | Lean et al. | |
| 2009/0053749 A1 | 2/2009 | Manalis et al. | |
| 2009/0114607 A1 | 5/2009 | Lean et al. | |
| 2009/0136982 A1 | 5/2009 | Tang et al. | |
| 2010/0314323 A1 | 12/2010 | Lean et al. | |
| 2010/0314327 A1 | 12/2010 | Lean et al. | |
| 2013/0011210 A1 | 1/2013 | Toner et al. | |
| 2013/0130226 A1 | 5/2013 | Lim et al. | |

FOREIGN PATENT DOCUMENTS

| | | |
|---|---|---|
| JP | 2007-268490 | 10/2007 |
| WO | WO 2007/021409 A1 | 2/2007 |
| WO | WO 2007/081902 A3 | 7/2007 |
| WO | WO 2015/057159 | 4/2015 |

OTHER PUBLICATIONS

Gossett D.R. et al., Label-free cell separation and sorting in microfluidic systems, Anal. Bioanal. Chem., 2010, vol. 397, pp. 3249-3267; published online on Apr. 25, 2010.*
Bhagat, A.A.S., "Inertial Microfluidics for Particle Separation and Filtration", Ph.D. thesis, College of Engineering, University of Cincinnati (Feb. 10, 2009).
Evans, E., et al., "Static and Dynamic Rigidities of Normal and Sickle Erythrocytes," *Journal of Clinical Investigation*, 73(2):477-488 (1984).
Rosenbluth, M.J., et al., "Force Microscopy of Nonadherent Cells: A Comparison of Leukemia Cell Deformability," *Biophysical Journal*, 90(8): 2994-3003 (2006).
Paulitschke, M., et al., "Membrane Rigidity of Red Blood Cells Parasitized by Different Strains of Plasmodium Falciparum," *Journal of Laboratory and Clinical Medicine*, 122(5): 581-589 (1993).
Suresh, S., et al., "Connections Between Single-Cell Biomechanics and Human Disease States: Gastrointestinal Cancer and Malaria," *Acta Biomaterialia*, 1(1): 15-30 (2005).

(Continued)

*Primary Examiner* — Satyendra K Singh
(74) *Attorney, Agent, or Firm* — Hamilton, Brook, Smith & Reynolds, P.C.

(57) ABSTRACT

A method of detecting one or more diseased blood cells in a blood sample includes introducing a blood sample into at least one inlet of a microfluidic device comprising one or more linear channels wherein each channel has a length and a cross-section of a height and a width defining an aspect ratio adapted to isolate diseased blood cells along at least one portion of the cross-section of the channel based on reduced deformability of diseased blood cells as compared to non-diseased blood cells, wherein diseased blood cells flow along a first portion of the channel to a first outlet and non-diseased blood cells flow along a second portion of the channel to a second outlet. The one or more channels can be adapted to isolate cells along portions of the cross-section of the channel based on cell size. In some embodiments, the one or more channels can be spiral channels.

7 Claims, 14 Drawing Sheets

(56) References Cited

OTHER PUBLICATIONS

Shelby, J.P., et al., "A Microfluidic Model for Single-Cell Capillary Obstruction by Plasmodium Falciparum-Infected Erythrocytes," *Proceedings of the National Academy of Sciences of the United States of America*, 100(25): 14618-14622 (2003).

Glenister, F.K., et al., "Contribution of Parasite Proteins to Altered Mechanical Properties of Malaria-Infected Red Blood Cells," *Blood*, 99(3):1060-1063 (2002).

Nash, G.B., et al., "Abnormalities in the Mechanical Properties of Red Blood Cells Caused by Plasmodium Falciparum," *Blood*. 74(2): 855-861 (1989).

Herricks, T., et al., "Deformability Limits of Plasmodium Falciparum-Infected Red Blood Cells," *Cellular Microbiology*. 11(9): 1340-1353 (2009).

Cranston, H.A., et al. "Plasmodium Falciparum Maturation Abolishes Physiologic Red Cell Deformability," *Science*. 223(4634): 400-403 (1984).

Marinkovic, M., et al., "Febrile Temperature Leads to Significant Stiffening of Plasmodium Falciparum Parasitized Erythrocytes," *American Journal of Physiology-Cell Physiology*. 296(1):C59-C64 (2009).

Notification of Transmittal of the International Search Report and the Written Opinion of the International Searching Authority, or the Declaration for International Application No. PCT/US2011/027276 (Date of Mailing May 13, 2011).

Sutton, N., et al., "A Novel Instrument for Studying the Flow Behaviour of Erythrocytes Through Microchannels Simulating Human Blood Capillaries," *Microvascular Research*, 53(3): 272-281 (1997).

Safeukui, I., et al., "Retention of Plasmodium Falciparum Ring-Infected Erythrocytes in the Slow, Open Microcirculation of the Human Spleen," *Blood*. 112(6):2520-2528 (2008).

Coupier, G., et al., "Noninertial Lateral Migration of Vesicles in Bounded Poiseuille Flow," *Physics of Fluids*. 20(11): 4 (2008).

Shevkoplyas, S.S., et al., "Direct Measurement of the Impact of Impaired Erythrocyte Deformability on Microvascular Network Perfusion in a Microfluidic Device," *Lab on a Chip*. 6(7): 914-920 (2006).

Fujiwara, H., et al., "Red Blood Cell Motions in High-Hematocrit Blood Flowing Through a Stenosed Microchannel," *Journal of Biomechanics*. 42(7): 838-843 (2009).

Ho, M., et al., "Visualization of *Plasmodium Falciparum*—Endothelium Interactions in Human Microvasculature: Mimicry of Leukocyte Recruitment," *Journal of Experimental Medicine*, 192(8): 1205-1211 (2000).

Xiaomi, T., et al., "Separation and Characterization of Red Blood Cells with Different Membrane Deformability Using Steric Field-flow Fractionation," *Journal of Chromatography B: Biomedical Sciences and Applications*. 674(1): 39-47 (1995).

Lincoln, B, et al., "Deformability-Based Flow Cytometry," *Cytometry Part A*. 59A(2): 203-209 (2004).

Vona, G., et al., "Enrichment, Immunomorphological, and Genetic Characterization of Fetal Cells Circulating in Maternal Blood," *American Journal of Pathology*, 160(1): 51-58 (2002).

Bhagat, A.A.S., et al., "Microfluidics for Cell Separation," *Medical and Biological Engineering and Computing*, 48: 999-1014 (2010).

Goldsmith, H.L., et al., "Margination of Leukocytes in Blood Flow Through Small Tubes," *Microvascular Research*. 27(2): 204-222 (1984).

Di Carlo, D., "Inertial Microfluidics," *Lab-on-a-chip*,. 9(21): p. 3038-3046 (2009).

Bhagat, A.A.S., et al., "Enhanced Particle Filtration in Straight Microchannels Using Shear-Modulated Inertial Migration," *Physics of Fluids*, 20: 101702 (4 pp) (2008).

Asmolov, E.S., "The Inertial Lift on a Spherical particle in a Plane Poiseuille Flow at Large Channel Reynolds Number," *Journal of Fluid Mechanics*, 381: 63-87 (1999).

Zeng, L., et al., "Wall-Induced Forces on a Rigid Sphere at Finite Reynolds Number," *Journal of Fluid Mechanics*, 536: 1-25 (2005).

Matas, J.P., et al., "Lateral Forces on a Sphere," *Oil & Gas Science and Technology*, 59(1): 59-70 (2004).

Segre, G. et al., "Radial Particle Displacements in Poiseuille Flow of Suspensions," *Nature*, 189: 209-210 (1961).

Segre, G. et al., "Behaviour of Macroscopic Rigid Spheres in Poiseuille Flow," *J. Fluid Mech*, 14: 115-136 (1962).

Matas, J.-P., et al., "Inertial Migration of Rigid Spherical Particles in Poiseuille Flow," *Journal of Fluid Mechanics*, 515: 171-195 (2004).

Bhagat, A.A.S., et al., "Continuous Particle Separation in Spiral MicroChannels Using Dean Flows and Differential Migration," *Lab on a chip*, 8(11): 1906-1914 (2008).

Hampton, R.E., et al., "Migration of Particles Undergoing Pressure-Driven Flow in a Circular Conduit," *Journal of Rheology*, 41(3): 621 (1997).

Fiebig, E, et al., "Rapid Leukocyte Accumulation by "Spontaneous" Rolling and Adhesion in the Exteriorized Rabbit Mesentery," *International Journal of Microcirculation Clinical and Experimental*. 10(2): 127-144 (1991).

Di Carlo, D., et al., "Continuous Inertial Focusing, Ordering, and Separation of Particles in Microchannels," *Proceedings of the National Academy of Sciences*, 104(48): 18892-18897 (2007).

Chun, B. et al., "Inertial Migration of Neutrally Buoyant Particles in a Square Duct: An Investigation of Multiple Equilibrium Positions," *Physics of Fluids*, 18: 031704 (4 pp) (2006).

Bhagat, A.A.S., et al., "Inertial Microfluidics for Continuous Particle Filtration and Extraction," *Microfluidics and Nanofluidics*, 7(2): 217-226 (2009).

Delamarche, E., et al., "Stability of Molded Polydimethylsiloxane Microstructures," *Advanced Materials*, 9(9): 741-746 (1997).

Xia, Y. et al., "Soft Lithography," *Annual Review of Materials Science*, 28(1): 153-184 (1998).

Kim, U., et al., "Selection of Mammalian Cells Based on Their Cell-Cycle Phase Using Dielectrophoresis," *Proceedings of the National Academy of Sciences*, 104(52): 20708 (2007).

Thevoz, P., et al., "Acoustophoretic Synchronization of Mammalian Cells in Microchannels," *Analytical chemistry* 82: 3094-3098 (2010).

Choi, S., et al., "Microfluidic Self-Sorting of Mammalian Cells to Achieve Cell Cycle Synchrony by Hydrophoresis," *Analytical chemistry*,.81(5): 1964-1968 (2009).

Migita, S., et al., "Cell Cycle and Size Sorting of Mammalian Cells Using a Microfluidic Device," *Analytical Methods*, 2: 657-660 (2010).

Yeh, C., et al., "Transient Lateral Transport of Platelet-Sized Particles in Flowing Blood Suspensions," *Biophysical Journal*, 66(5): 1706-1716 (1994).

Pries, A.R., et al., "Biophysical Aspects of Blood Flow in the Microvasculature," *Cardiovascular Research*. 32(4): 654-667 (1996).

McDonald, J.C., et al., "Poly(dimethylsiloxane) as a Material for Fabricating Microfluidic Devices," *Accounts of Chemical Research*. 35(7): 491-499 (2002).

Bhagat A.A.S., et al., "Enhancing Particle Dispersion in a Passive Planar Micromixer Using Rectangular Obstacles," *Journal of Micromechanics and Microengineering*. 18(8): 085005 (9 pp) (2008).

Jain, A., et al., "Determinants of Leukocyte Margination in Rectangular Microchannels," *PLoS One*. 4(9):e7104 (8 pp) (2009).

Zhao, R., et al., "Micro-Flow Visualization of Red Blood Cell-Enhanced Platelet Concentration at Sudden Expansion," *Annals of Biomedical Engineering*. 36(7): 1130-1141 (2008).

Demirev, P.A., et al. "Detection of Malaria Parasites in Blood by Laser Desorption Mass Spectrometry," *Analytical Chemistry*. 74(14): 3262-3266 (2002).

Gascoyne, P., et al. "Microsample Preparation by Dielectrophoresis: Isolation of Malaria," *Lab on a Chip* 2(2): 70-75 (2002).

Dondorp, A.M., et al., "Abnormal Blood Flow and Red Blood Cell Deformability in Severe Malaria," *Parasitology Today*. 16(6): 228-232 (2000).

Cooke, B.M., et al., "Falciparum Malaria: Sticking Up, Standing Out, and Out-Standing," *Parasitology Today*. 16(10): 416-420 (2000).

(56) References Cited

OTHER PUBLICATIONS

Popel, A.S. et al., "Microcirculation and Hemorheology," *Annual Review of Fluid Mechanics*. 37: 43-69 (2005).
Zimmerman, P.A., et al., "Diagnosis of Malaria by Magnetic Deposition Microscopy," *American Journal of Tropical Medicine and Hygiene*. 74(4): 568-572 (2006).
Goldsmith, H.L., et al., "Robin Fåhraeus: Evolution of his Concepts in Cardiovascular Physiology," *American Journal of Physiology*. 257(3): H1005-H1015 (1989).
Karl, S., et al., "Enhanced Detection of Gametocytes by Magnetic Deposition Microscopy predicts higher potential for Plasmodium Falciparum Transmission," *Malaria Journal*. 7(1): 66 (2008).
Stevens, D.Y., et al., "Enabling a Microfluidic Immunoassay for the Developing World by Integration of On-Card Dry Reagent Storage," *Lab on a Chip*. 8(12): 2038-2045 (2008).
Wersto, R.P., et al., "Doublet Discrimination in DNA Cell-Cycle Analysis," *Cytometry Part B: Clinical Cytometry*, 46(5): 296-306 (2001).
Russom, A., et al., "Differential Inertial Focusing of Particles in Curved Low-Aspect-Ratio Microchannels," *New Journal of Physics*,11: 075025 (9 pp) (2009).
Kuntaegowdanahalli, S.S., et al., "Inertial Microfluidics for Continuous Particle Separation in Spiral Microchannels," *Lab on a Chip*, 2009. 9(20): 2973-2980.
Cooper, S., "Rethinking Synchronization of Mammalian Cells for Cell Cycle Analysis," *Cellular and Molecular Life Sciences*, 60(6): 1099-1106 (2003).
Whitfield, M.L., et al., "Identification of Genes Periodically Expressed in the Human Cell Cycle and Their Expression in Tumors," *Molecular Biology of the Cell*, 2002. 13(6): 1977-2000 (2002).
Hou, H.W., et al., "Deformability Based Cell Margination—A Simple Microfluidic Design for Malaria-Infected Erythrocyte Separation," *Lab on a chip*, 10(19): 2605-2613 (2010).
Gupta, A, et al., "Effect of Aspect Ratio on Inertial Migration of Neutrally Buoyant Spheres in a Rectangular Channel," *47th AIAA Aerospace Sciences Meeting*, Orlando, FL (Jan. 5-8, 2009).
Yamada, M., et al., "Pinched Flow Fractionation: Continuous Size Separation of Particles Utilizing a Laminar Flow Profile in a Pinched Microchannel," *Anal. Chem.*, 76(18): 5465-5471 (2004).
Fan, R, et al., "Integrated Barcode Chips for Rapid, Multiplexed Analysis of Proteins in Microliter Quantities of Blood," *Nature Biotechnology*. 26(12): 1373-1378 (2008).
Tan, S.J., et al., "Microdevice for the Isolation and Enumeration of Cancer Cells from Blood," *Biomedical Microdevices*, 11(4): 883-892 (2009).
Lincoln, B., et al., "Deformability-Based Flow Cytometry," *Cytometry Part A*, 59(2): 203-209 (2004).
Hou, H.W., et al., "Deformability Study of Breast Cancer Cells Using Microfluidics," *Biomedical Microdevices*, 11(3): p. 557-564 (2009).
Born, C., et al., "Estimation of Disruption of Animal Cells by Laminar Shear Stress," *Biotechnology and Bioengineering*, 40(9): p. 1004-1010 (1992).
Sethu, P., et al., "Microfluidic Diffusive Filter for Apheresis (Leukapheresis)," *Lab on a Chip*, 6(1): p. 83-89 (2006).
Schmid-Schonbein, G.W., et al., "Morphometry of Human Leukocytes," *Blood*, 56(5): 866-875 (1980).
Downey, G.P., et al., "Retention of Leukocytes in Capillaries: Role of Cell Size and Deformability," *Journal of Applied Physiology*, 69(5): 1767-1778 (1990).

Lara, O., et al.,"Enrichment of Rare Cancer Cells Through Depletion of Normal Cells Using Density and Flow-Through, Immunomagnetic Cell Separation," *Experimental hematology*, 32(10): 891-904 (2004).
Nagrath, S., et al., "Isolation of Rare Circulating Tumour Cells in Cancer Patients by Microchip Technology," *Nature*, 450(7173): 1235-1239 (2007).
Mohamed, H., et al., "Isolation of Tumor Cells Using Size and Deformation," *Journal of Chromatography A*, 1216(47): 8289-8295 (2009).
Jäggi, R.D., et al., "Microfluidic Depletion of Red Blood Cells from Whole Blood in High-Aspect-Ratio Microchannels," *Microfluidics and Nanofluidics*. 3(1): 47-53 (2007).
Zheng, S., et al., "Membrane Microfilter Device for Selective Capture, Electrolysis and Genomic Analysis of Human Circulating Tumor Cells," *Journal of Chromatography A*, 1162(2): 154-161 (2007).
Zabaglo, L., et al., "Cell Filtration—Laser Scanning Cytometry for the Characterisation of Circulating Breast Cancer Cells," *Cytometry Part A*, 55(2): 102-108 (2003).
Paterlini-Brechot, P. and Benali, N.L.,"Circulating Tumor Cells (CTC) Detection: Clinical Impact and Future Directions," *Cancer letters*, 253(2): p. 180-204 (2007).
Gleghorn, J.P., et al., "Capture of Circulating Tumor Cells from Whole Blood of Prostate Cancer Patients Using Geometrically Enhanced Differential Immunocapture (GEDI) and a Prostate-Specific Antibody," *Lab on a Chip*, 10(1): 27-29 (2010).
Adams, A.A., et al., "Highly Efficient Circulating Tumor Cell Isolation from Whole Blood and Label-Free Enumeration Using Polymer-Based Microfluidics with an Integrated Conductivity Sensor," *Journal of the American Chemical Society*, 130(27): 8633-8641 (2008).
Shevkoplyas, S.S., et al., "Biomimetic Autoseparation of Leukocytes from Whole Blood in a Microfluidic Device," *Analytical Chemistry*. 77(3): 933-937 (2005).
Notification Concerning Transmittal of International Preliminary Report on Patentability for International Application No. PCT/US2011/027276 filed Mar. 4, 2011.
Schaff, U.Y., et al., "Vascular Mimetics Based on Microfluidics for Imaging the Leukocyte-Endothelial Inflammatory Response," *Lab-on-a-Chip*, 7:448-456 (2007).
Zheng, S., et al., "Streamline-Based Microfluidic Device for Erythrocytes and Leukocytes Separation," *Journal of Microelectromechanical Systems*, 17(4): 1029-1038 (2008).
Toner, M. and Irimia, D., "Blood-on-a-Chip," *Annual Review of Biomedical Engineering*, 7:77-103 (2005).
Chin, C.D., et al., "Lab-on-a-Chip Devices for Global Health: Past Studies and Future Opportunities," *Lab-on-a-Chip*,7:41-57 (2007).
Lee, S.S., et al., "Extensional Flow-Based Assessment of Red Blood Cell Deformability Using Hyperbolic Converging Microchannel," *Biomedical Microdevices*, (2009).
Antia, M., et al., "Microfluidic Approaches to Malaria Pathogenesis," *Cellular Microbiology*, 10(10): 1968-1974 (2008).
Price, A.K., et al., "Monitoring Erythrocytes in a Microchip Channel that Narrows Uniformly: Towards an Improved Microfluidic-Based Mimic of the Microcirculation," *Journal of Chromatography A*, 1111(2): 220-227 (2006).
International Search Report and Written Opinion for PCT/SG2013/000442 dated Feb. 10, 2014.

* cited by examiner

Figure 7A
Figure 7B
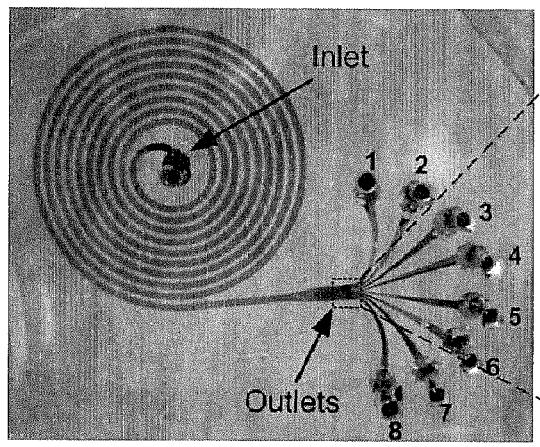
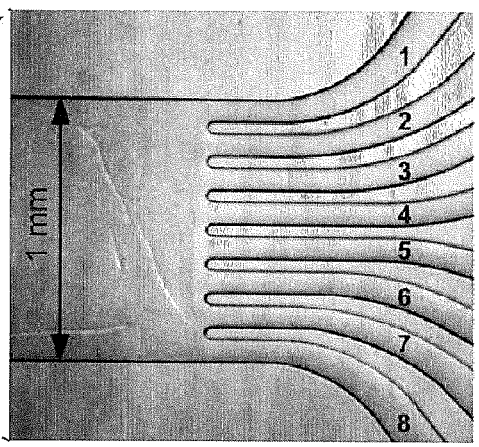
Figure 8
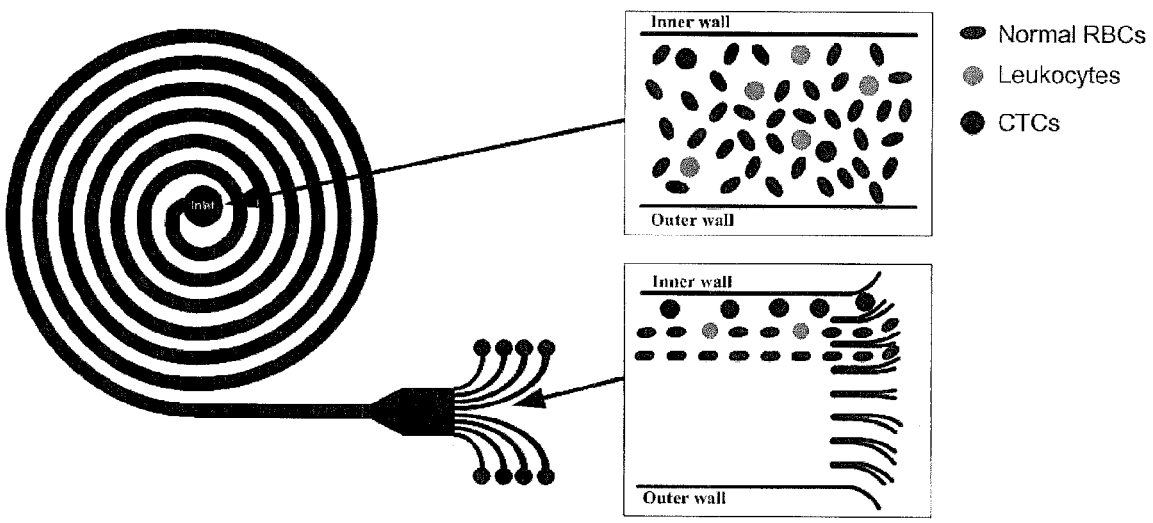

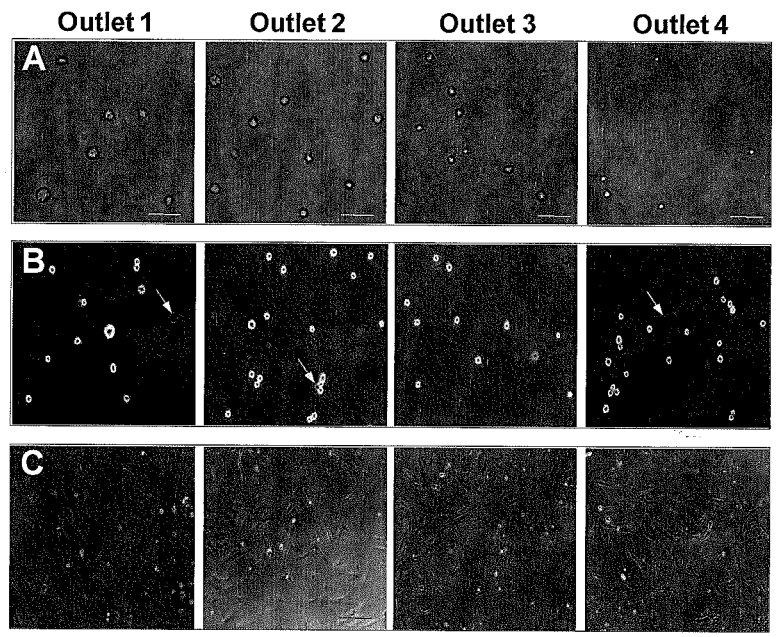
Figure 11A
Figure 11B
Figure 11C
Figure 12
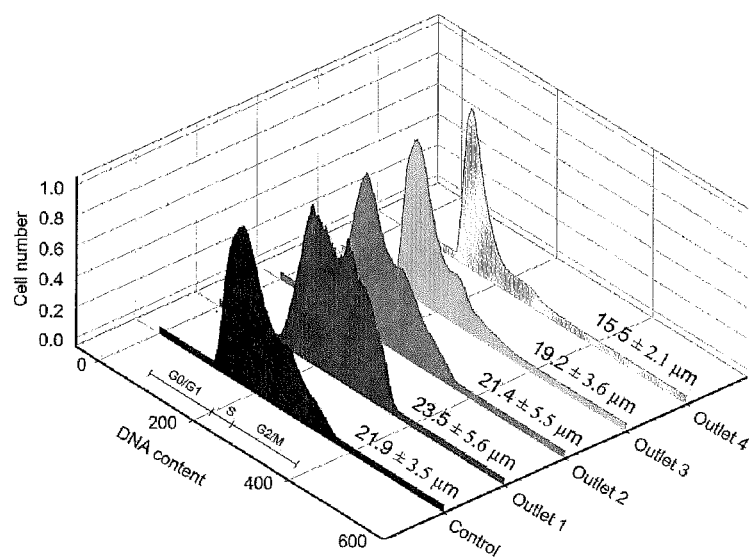

Figure 14
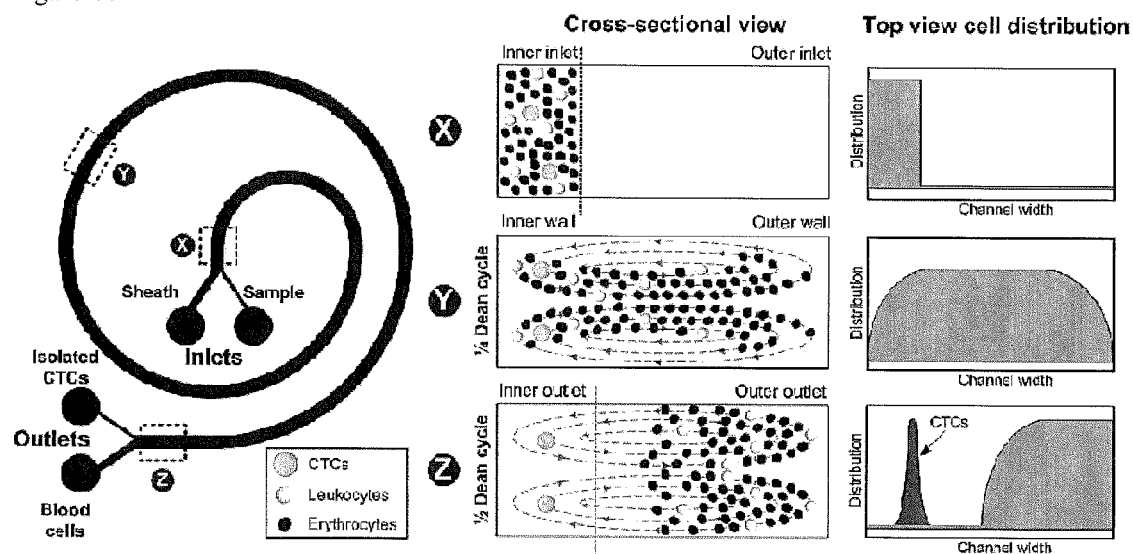
Figure 15A
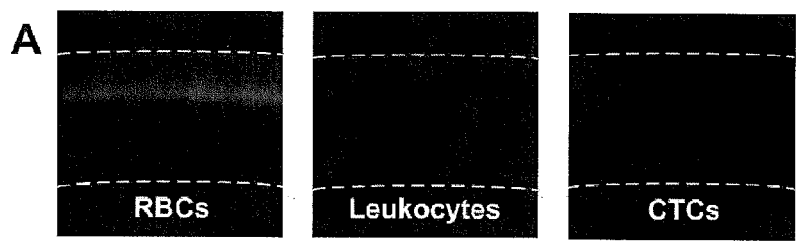
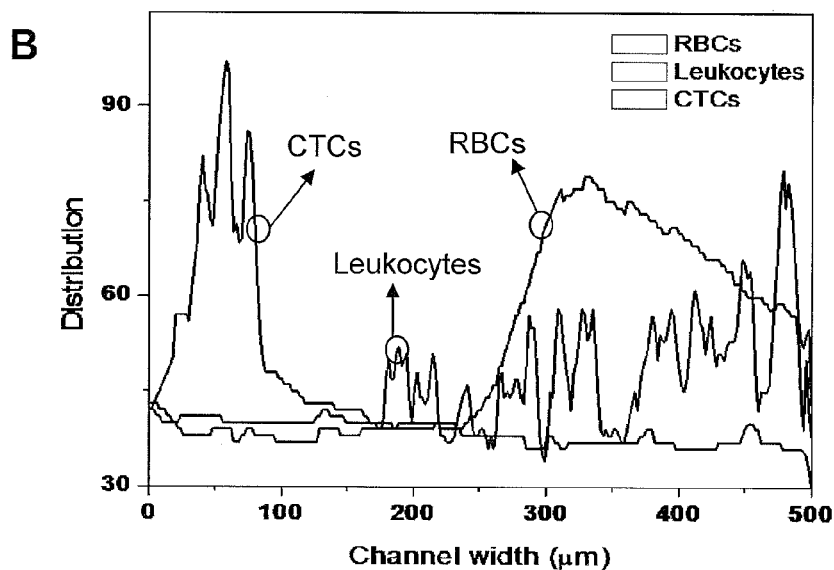
Figure 15B

Figure 18A        Figure 18B        Figure 18C
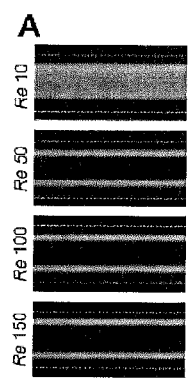 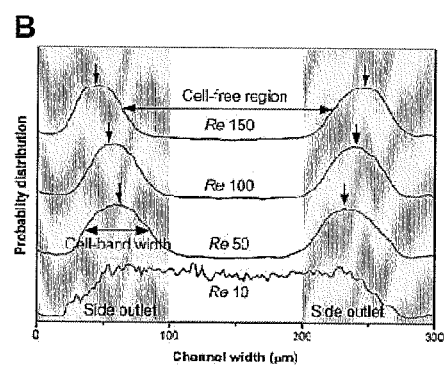 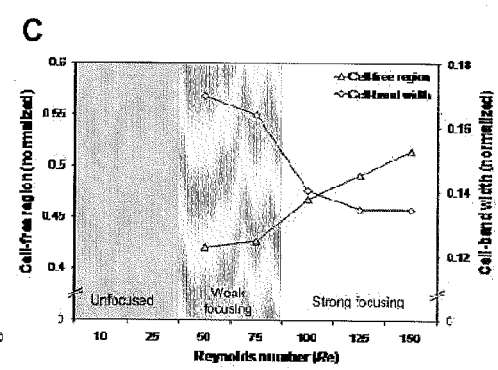
Figure 19A        Figure 19B        Figure 19C
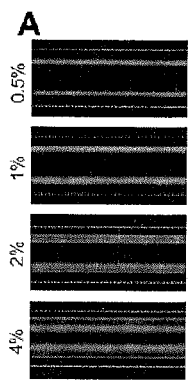 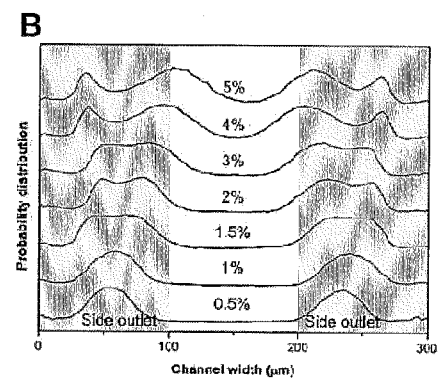 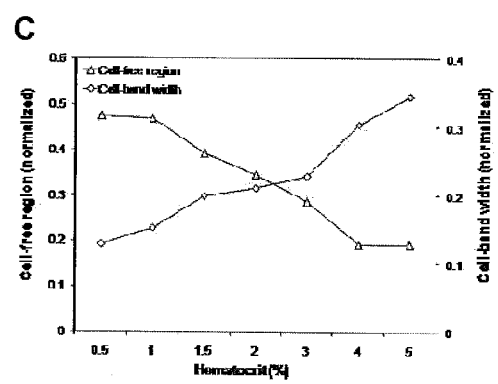

MICROFLUIDICS SORTER FOR CELL DETECTION AND ISOLATION

RELATED APPLICATION(S)

This application is the U.S. National Stage of International Application No. PCT/US2011/027276, filed Mar. 4, 2011, which designates the U.S., published in English, and claims the benefit of U.S. Provisional Application No. 61/310,387, filed on Mar. 4, 2010 and U.S. Provisional Application No. 61/383,881 filed on Sep. 17, 2010. The entire teachings of the above application(s) are incorporated herein by reference.

BACKGROUND OF THE INVENTION

Convectional macroscale methods for separation of cells include physical filtration using membrane-based filter and density gradient centrifugation which exploit differences in cell size, deformability, and density to filter out target cells. These techniques are labor-intensive and require multi-step sample preparations which may introduce artifacts or lead to loss of desired cells. Membrane filtration methods are also easily susceptible to clogging and require frequent cleaning. Further, evidence of mechanical stress-induced changes in original phenotype of target cells subjected to filtration and centrifugation techniques has also been reported.

Hence, there is a clear need to develop simpler and more efficient techniques to process blood samples that can minimize cell loss and maintain the original target cell phenotype for subsequent analysis.

SUMMARY OF THE INVENTION

Microfluidics is particularly well suited for processing blood samples primarily because of its small length scale which allows better control of the cellular microenvironment during blood separation. On-chip blood analysis has been demonstrated by several groups for different applications such as study of RBCs deformability, separation of platelets and plasma, separation of leukocytes and isolation of rare cells such as CTCs or fetal cells from blood. However, a major limitation in these microfluidics systems is the low processing throughput, either due to sample dilution or to slow flow rates, making them unsuitable for processing clinical blood samples which are usually milliliters in volume. Described herein are microfluidic devices which overcome these problems.

Accordingly, the invention is generally directed to methods of detecting a (one or more) cell in a sample. In a particular aspect, the invention is directed to a method of detecting one or more diseased blood cells in a blood sample (e.g., whole blood). The method includes introducing a blood sample into at least one inlet of a microfluidic device comprising one or more linear channels wherein each channel has a length and a cross-section of a height and a width defining an aspect ratio adapted to isolate diseased blood cells along at least one portion of the cross-section of the channel based on reduced deformability of diseased blood cells as compared to non-diseased blood cells, wherein diseased blood cells, if present, flow along a first portion of the channel to a first outlet and non-diseased blood cells flow along a second portion of the channel to a second outlet, thereby detecting one or more diseased blood cells in the sample.

In another aspect, the invention is directed to a method of detecting one or more circulating tumor cells (CTCs) in a sample of an individual, which includes introducing the sample into at least one inlet of a microfluidic device comprising one or more spiral channels wherein each channel has a length and a cross-section of a height and a width defining an aspect ratio adapted to isolate circulating tumor cells along portions of the cross-section of the channel based on cell size, wherein the circulating tumor cells, if present, flow along the radially innermost portion of the channel to a first outlet and other cells in the sample flow along another portion of the channel to a second outlet, thereby detecting one or more circulating tumor cells in the sample of the individual.

In yet another aspect, the invention is directed to a method of isolating one or more synchronized cells from an asynchronous cell mixture (e.g., suspension). The method includes introducing an asynchronous cell mixture into at least one inlet of a microfluidic device comprising one or more spiral channels wherein each channel has a length and a cross-section of a height and a width defining an aspect ratio adapted to isolate synchronized cells along portions of the cross-section of the channel based on cell size, wherein larger synchronized cells flow along the radially innermost portion of the channel to a first outlet and smaller synchronized cells flow along other portions of the channel to at least one other outlet, thereby isolating one or more synchronized cells from the asynchronous cell mixture.

In still another aspect, the invention is directed to a method of detecting one or more circulating tumor cells (CTCs) in a sample of an individual. The method includes introducing the sample into at least one inlet of a microfluidic device comprising one or more linear channels, wherein each channel has a length and a cross-section of a height and a width defining an aspect ratio adapted to isolate circulating tumor cells along at least one portion of the cross-section of the channel based on cell size, wherein circulating tumor cells, if present, flow along the first portion of the channel to a first outlet and other cells in the sample flow along a second portion of the channel to a second outlet, thereby detecting one or more CTCs in the sample of the individual.

This invention has many advantages, including continuous operation at a relatively high flow rate, enabling faster processing of clinical samples, with no chemical modification of the sample, which reduces processing time and cost, and the collection of viable cells for subsequent biological assays.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIGS. 7A and 7B are photographs of the fabricated spiral microchannel for CTCs isolation with a single inlet and eight equally divided outlets (labeled 1-8) fabricated in PDMS (the microchannel is filled with dye for visualization). Also shown in FIG. 7A is a microscopic image illustrating the outlet section of the spiral microchannel.

FIG. 8 is a schematic illustration of the spiral sorter for CTCs isolation. At the inlet, the blood cells (RBCs, leukocytes and CTCs) are randomly distributed across the microchannel cross-section. Under the influence of the inertial lift force and the Dean vortices, these cells equilibrate at distinct positions within the cross-section based on their size, with the larger CTCs equilibrating closest to the inner microchannel wall. The individual cell streams are then extracted using eight equally spaced outlets, achieving separation.

FIGS. 9A and 9B are illustrations, wherein FIG. 9A is a schematic illustration of the spiral microfluidic design developed for cell cycle synchronization. Under the influence of inertial lift forces and Dean drag force, asynchronous cell populations are size fractionated to obtain relatively pure populations of cells in the G0/G1, S and G2/M phase. The cells in the G2/M phase, due to the large size, equilibrate closest to the microchannel inner wall followed by cells in the S and the G0/G1 phase; the inset is a photograph of the spiral microchannel with one inlet and eight outlets fabricated in PDMS; 9B is a illustration of a validation of the design principle using fluorescently labeled polystyrene particles. Superimposed images illustrating the distribution and position of the 10 μm, 15 μm, and 25 μm diameter particles at the inlet, a 500 μm wide channel section prior to the outlet, and the bifurcated outlet of a 140 μm high microchannel at 2.5 ml/min flowrate. The randomly distributed particles at the inlet form ordered focused streams which are then collected separately at outlets 1, 2 and 3.

FIGS. 11A-11C are optical micrographs of the size sorted hMSCs cells collected from outlets 1, 2, 3 and 4. 11A shows that the mean cell diameter collected at outlet 1 is ~24 μm as compared to ~15 μm collected at outlet 4. ($p<0.001$). 11B shows trypan-blue stained micrographs of collected cells indicating viability of hMSCs post sorting (arrows indicate the non-viable cells). Results indicate that the high shear experienced by the cells in these microchannels do not compromise their viability, achieving >90% cell recovery. 11C is a optical micrograph of the re-seeded cells indicating no significant difference between the proliferation rate of cells collected from the outlets indicating high viability and sterility; bar=50 μm.

FIG. 12 shows histograms indicating the distribution of the DNA content of the sorted hMSCs in the G0/G1, S and G2/M phase post synchronization. The size distributions of the synchronized cells are also indicated on the plot ($p<0.05$).

FIG. 14 is a schematic of the developed ultra-high throughput CTC isolation chip illustrating the operating principle. Whole blood is pumped through the inner inlet of the device while sheath fluid is passed through the outer inlet. Under the influence of Dean drag forces, due to the curvilinear channel geometry, the smaller hematologic cells (RBCs and WBCs) migrate out towards the channel outer wall following the two counter rotating vortices (cross-sectional view). The CTCs, due to their larger size. experience strong inertial lift forces equilibrating them along the microchannel inner wall, thus achieving separation.

FIGS. 15A and 15B are average composite images 15A and linescans 15B, indicating the lateral positions of the RBCs, leukocytes and CTCs at the outlet of the spiral microchannel. The images show that the hematologic cells (RBCs and leukocytes) are transposed to the outer half of the channel under the influence of Dean drag forces while the larger CTCs focus closer to the channel inner wall under the influence of inertial lift forces.

FIGS. 18A-18C show the effect of flowrate (Re) on red blood cell focusing. 18A Averaged composite images illustrating RBC equilibration for increasing flowrate. The input blood sample was fixed at 1% hematocrit and pumped through AR 5 microchannel (dotted lines indicate approximate position of channel walls). 18B Linescans representing the probability distribution of RBCs across the microchannel width measured at the outlet. 18C Experimental result indicating the width of the cell-free region at the channel center and the thickness of the cell-band for increasing Reynolds number (Re).

FIGS. 19A-19C show the effect of hematocrit on red blood cell focusing. 19A Averaged composite images illustrating RBC equilibration for increasing hematocrit. The input blood sample was pumped at Re=100 through AR 5 microchannel (dotted lines indicate approximate position of channel walls). 19B Linescans representing the probability distribution of RBCs across the microchannel width measured at the outlet. 19C Experimental result indicating the width of the cell-free region at the channel center and the thickness of the cell-band for increasing hematocrit.

DETAILED DESCRIPTION OF THE INVENTION

Figure 1A:
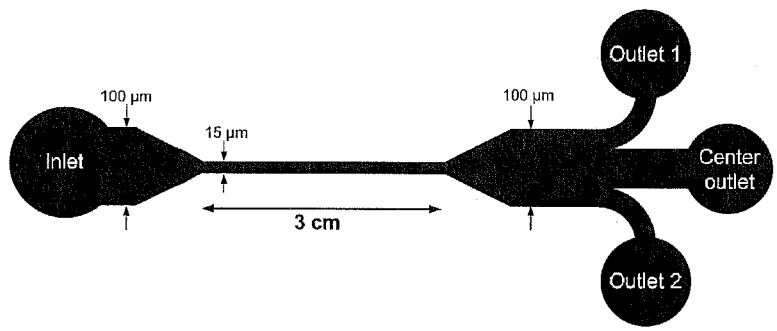
FIGS. 1A and 1B are schematic illustrations of the microchannel design and separation principle of the invention. 1A Schematic of one example of a microfluidic design illustrating the device dimensions. In this device, the microchannels comprise a 100 µm wide segment at the input that constricts to 15 m. At the outlet, the microchannel opened into a 100 µm wide section for enhanced visualization with a 3-outlet bifurcation divided in 1:2:1 ratio. The microchannel height was fixed at 10 µm. 1B Schematic of the cross-sectional and top view of the microchannel illustrating the separation principle. The randomly distributed infected red blood cells (iRBCs) at the microchannel inlet marginate to the channel sidewalls as the flow reaches the outlet and are filtered out using a three outlet system.

A description of example embodiments of the invention follows.

The invention is generally directed to microfluidic devices and the use of such devices to detect and/or isolate one or more particular type of cell (e.g., target cell(s) to be detected and/or isolated) from a sample comprising 2 or more (multiple) cell types (e.g., a collection or mixture of cells). The microfluidic device comprises one or more inlets for introduction of the sample, one or more channels through which the sample flows, and one or more outlets, and typically at least two outlets, wherein the cells to be detected in the sample and/or isolated flow through one of the outlets (e.g., a first outlet), and the remainder of the cells in the sample do not flow through the same outlet as the cells to be isolated do, and/or flow through another (distinct) outlet (e.g., a second outlet). Each one or more channels has a length and a cross section of a height and a width defining an aspect ratio adapted to isolate the target cell(s) along at least one portion of the cross section of the channel, wherein the target cell(s) flow along a first portion of each channel to a first outlet and the remaining cells flow along a second portion of each channel and do not flow through the same outlet as the target cell(s) and/or flow through one or more (distinct e.g., a second, third, fourth, fifth, sixth, seventh, eight, etc.) outlets.

As described herein, the microfluidic device can have one or more (at least one) inlet for introduction of the sample into the device. For example, the device can have one, two, three, four, five, six, seven, eight, nine, ten, etc., inlets.

The sample can be introduced into the device using a variety of techniques known to those of ordinary skill in the art. For example, the sample can be introduced using a syringe and/or a pump.

Similarly, the microfluidic device can have one or more outlets. In some aspects, the device can have one, two, three, four, five, six, seven, eight, nine, ten, etc., outlets. In a particular aspect, the device has at least 2 outlets. In another aspect, the device has 3 outlets. In yet another aspect, the device has 4 outlets. In still another aspect, the device has 8 outlets.

The device also comprises one or more channels (e.g., parallel channels, for example one, two, three, four, five, six, seven, eight, nine, ten, etc., parallel channels) connecting the one or more inlets to the one or more outlets. The channel(s) comprise a cross section of a height and a width defining an aspect ratio that enables separation of the target cell(s) from the remainder of the cells in the sample. As used herein, an aspect ratio is the ratio of a channel's height divided by its width and provides the appropriate cross section of the channel to allow the target cells to flow along at least one portion of the cross section of the channel to a first outlet, and the remaining cells to flow along a different (e.g., second, third, fourth, etc.) part or cross section of the channel and not to the same outlet as the target cells, such as to a distinct (e.g., second, third, fourth, etc.) outlet. The appropriate aspect ratio causes the target cells to flow along a distinct portion of the channel based on a difference in a structural characteristic of the target cell in the sample, compared to the same or similar structural characteristic of the remaining cells in the sample. Examples of such structural characteristics include cell size, stiffness, deformability, adhesiveness (e.g., cytoadhesiveness), and the like. For example, as shown herein, aspect ratios of 1, 2.5, 3.75, 5, or 7 can be used.

As will be appreciated by those of ordinary skill in the art, the channel can have a variety of shapes. In some aspects, the channel can be linear. The height of the linear channel can be in a range of between about 10 µm and about 200 µm, such as about 20 µm, about 50 µm, about 75 µm, about 100 µm, and about 150 µm. The width of the linear channel can be in a range of between about 10 µm and about 50 µm, such as about 12 µm, about 15 µm, and about 20 µm. The length of the linear channel can be in a range of between about 1 cm and about 5 cm, such as about 3 cm.

In other aspects, the channel is curved. In a particular aspect the channel is a spiral. The height of the spiral channel can be in a range of between about 10 µm and about 200 µm, such as about 100 µm and about 140 µm. The width of the spiral channel can be in a range of between about 100 µm and about 500 µm. The length of the spiral channel can be in a range of between about 1 cm and about 10 cm.

The sample can flow through the microfluidic device at a variety of flow rates, for example physiological flow rate (e.g., physiological arteriole flow rate), or non-physiological flow rate. Example flow rates include about 20 million cells/min, or in a range of between about 2.5 mL/min and about 5 µL/min.

The microfluidic device described herein can be used to detect, separate, and/or isolate a target cell(s) from a sample of cells. The sample of cells can be, for example, a biological sample, such as blood (e.g., whole blood), plasma, peritoneal fluid, lymph, spinal fluid, urine, tissue, and the like. The sample can also be a cell culture sample. In a particular aspect, the sample is a blood sample (e.g., a whole blood sample). The blood sample can have a low hematocrit (e.g., about 1-10%), or a high hematocrit (e.g., about 20-50%).

Blood is a complex suspension of cells (~40-45% of blood volume) in plasma, which plays several key roles including transport of oxygen and nutrients to cells, removal of cellular waste products and providing immunological protection. Red blood cells (RBCs) make up for >99% of all hematologic cellular components (~$5 \times 10^9$ RBCs per milliliter of whole blood) with the remaining <1% consisting of peripheral blood leukocytes (PBL) and platelets. Due to its complex nature, analyzing blood using microfluidic biochips has been a challenging problem. In addition to RBCs and leukocytes, other low abundance cells such as fetal nucleated red blood cells, circulating tumor cells (CTCs), stem cells and leukemic cells are also found in the peripheral blood of patients which can be used for various biomedical applications such as patient monitoring, disease diagnosis, therapeutic treatment monitoring and conducting fundamental scientific studies. However, because these cells are extremely rare, an enrichment or separation step is almost always necessary to efficiently isolate them from blood prior to analysis.

Thus, one or more microfluidic devices (e.g., a cascade of microfluidic devices, e.g., in parallel or in sequence) described herein can be used for a variety of purposes, and, in one aspect, to detect separate and/or isolate a variety of target cells. A variety of target cells can be detected. Examples include diseased cells (e.g., diseased blood cells such as malaria-infected red blood cells, leukemic red blood cells, sickle cell anemia red blood cells, or a combination thereof, synchronized cells in an asynchronous mixture, and circulating tumor cells (CTCs)).

In one aspect, the device is used in a method of detecting one or more diseased blood cells in a blood sample. The method includes introducing a blood sample into at least one inlet of a microfluidic device comprising one or more linear channels wherein each channel has a length and a cross-section consisting of a height and a width defining an aspect ratio adapted to isolate diseased blood cells along at least one portion of the cross-section of the channel based on reduced deformability of diseased blood cells as compared to non-diseased blood cells, wherein diseased blood cells flow along a first portion of each channel to a first outlet and non-diseased blood cells flow along a second portion of each channel to a second outlet. As used herein, diseased cells are structurally different in one or more aspects as compared to non-diseased (e.g., healthy) cells. For example, diseased cells can be of a different size, stiffness, deformability, adhesiveness, or a combination thereof than the non-diseased cells. For example, the diseased cells can be malaria-infected red blood cells, sickle cell anemia red blood cells, leukemic red blood cells, or a combination thereof. In one aspect, the diseased cells can be early stage (e.g., ring stage), or late stage (e.g., trophozoite stage or schizont stage) malaria-infected red blood cells. The blood sample can be introduced at a flow rate of about 5 µL/min. In one aspect, the ring stage malaria-infected red blood cells can be separated with an efficiency in a range of between about 75% and about 85%. In another aspect, the late stage malaria-infected red blood cells can be separated with an efficiency of about 90%. The method can further include collecting diseased cells from the first outlet. In some embodiments, the aspect ratio of the channel can be in a range between about 1 and about 2. In certain embodiments, the microfluidic device can further include an expansion region for improved visualization. In some embodiments, the width of the second outlet can be in a range between about 2 and about 10 times wider than the width of the first outlet. In certain embodiments, the width of the channel can be about 15 µm. In some embodiments, the height of the channel can be about 10 µm.

As discussed above, in a particular aspect, the diseased cells are malaria-infected red blood cells. Malaria is one of the most severe parasitic diseases with half of the world's population (3.3 billion) at risk and an estimated 1 to 2 million deaths annually. Lack of resources in poorer countries further worsens the situation by imposing a major economic burden to tackle the disease in these affected countries. Of the four types of human malaria species, *Plasmodium* (*P.*) *falciparum* is the most deadly. Upon infection, *P. falciparum*-infected red blood cells (iRBCs) undergo various developmental stages (ring, trophozoite and schizont stages) in a 48-hour intraerythrocytic cycle. During this period, the parasites continuously remodel the host RBCs and export certain parasitic proteins that make iRBCs membranes more adhesive, thereby promoting cytoadherence and a progressive stiffening of iRBCs membrane as the parasites mature. These parasite-induced morphological changes compromise microcirculation, and can even manifest into pathophysiological outcomes such as anaemia, metabolic acidosis or organ failure in the case of severe malaria.

In one aspect, a deformability-based separation method for infected red blood cells (iRBCs) separation in a microfluidic device is described herein, inspired by the in vivo phenomenon of leukocyte margination (Goldsmith H L et al., (1984) *Microvascular Research*. 27(2): 204-222); (Fiebig E, et al., (1991) *International Journal of Microcirculation Clinical and Experimental*. 10(2): 127-144). In blood vessels with luminal diameter of less than about 300 µm, RBCs which are smaller in size and more deformable than the leukocytes, tend to migrate to the axial centre of the vessel, resulting in a formation of a reduced hematocrit plasma layer adjacent to the vessel wall and an increased red blood cell (RBC) concentration at the centre of the vessel (Pries A R, et al., (1996) *Cardiovascular Research*. 32(4): 654-667). This inward RBC migration is attributed to Poiseuille flow profile within the vessel which results in a pressure-gradient-induced force directed towards the centre (Goldsmith H L, et al., (1989) *American Journal of Physiology*. 257(3): H1005-H1015). Due to the parabolic fluid velocity profile in the vessel, with maximum at the centre, the bulk flow of RBCs at the axial centre get discharged faster. This gives rise to a decrease in tube hematocrit discharge, the Fahraeus effect, and also leads to a reduction in the apparent blood viscosity due to the presence of the cell-depleted plasma layer (Fahraeus-Lindqvist effect). Id. As the RBCs migrate towards the axial centre, mechanical collisions between the leukocytes and the migrating RBCs result in the larger (and less deformable) leukocytes being displaced to the vessel wall, a phenomenon aptly termed as margination (Goldsmith H L et al., (1984) *Microvascular Research*. 27(2): 204-222) and (Fiebig E, et al., (1991) *International Journal of Microcirculation-Clinical and Experimental*. 10(2): 127-144). These two hemodynamic effects, the Fahraeus effect and margination, have been employed in microfluidic devices for plasma separation (Fan R, et al. (2008) *Nature Biotechnology*. 26(12): 1373-1378) and (Jaggi R D, et al., (2007) *Microfluidics and Nanofluidics*. 3(1):47-53) and leukocyte enrichment from whole blood (Shevkoplyas S S, et al., (2005) *Analytical Chemistry*. 77(3): 933-937). In these previous examples, cells to be separated were significantly different from RBC, both in deformability (stiffness) and size. However, described herein is the application of this bio-mimetic separation technique for separating normal and malaria infected iRBCs, with the same sizes and only a subtle difference in cell deformability.

The separation principle was first demonstrated by using hard fluorescently labeled polystyrene 3 µm beads suspended in whole blood. Tests were then conducted using both ring stage and late trophozoite/schizont stage iRBCs mixed with whole blood. The results herein indicate a separation efficiency of about 75% for ring stage iRBCs and >90%, such as up to about 99%, for late stages iRBCs.

The separation technique described here does not require fluorescent dyes or other chemical modifications, and can be performed directly on the raw blood sample with high hematocrit number (~40%). A high hematocrit is a hematocrit in a range of between about 20% and about 50%, and, in particular aspects, about 30%, or about 40%. In one aspect, the microfluidic device is a one-inlet-three-outlet device, with a flow rate that allows easy interfacing with downstream detection techniques such as Giemsa staining. The operation of the device does not require electricity or batteries, and gravity-fed pumping could be used. All these features make this an ideal iRBCs enrichment technique for on-site testing in resource-limited clinical settings. In addition, it can be readily applied to other blood cell diseases (such as sickle cell anemia and leukemia), which are also characterized by changes in cell stiffness (Evans E, et al., (1984) *Journal of Clinical Investigation*, 73(2):477-488); (Rosenbluth M J, et al., (2006) *Biophysical Journal*, 90(8): 2994-3003).

Changes in iRBCs rigidity as the parasite matures within have been extensively studied (Paulitschke M et al., (1993) *Journal of Laboratory and Clinical Medicine*, 122(5):581-589); (Suresh S, et al., (2005) *Acta Biomaterialia*, 1(1):15-30); (Shelby J P, et al., (2003) *Proceedings of the National Academy of Sciences of the United States of America*, 100(25):14618-14622). Suresh et al., used optical tweezers to stretch and measure the elastic modulus of individual iRBCs at different stages of infection. The elastic modulus for uninfected RBCs, ring, trophozoite and schizont stages iRBCs reported were about 8, 16, 21.3 and 53.3 µN/m respectively (Sures S, et al. (2005) *Acta Biomaterialia*. 1(1):15-30). This significant change in cell stiffness between the various stages is partly attributed to the presence of the large and nondeformable parasites residing within the cells, resulting in a large increase in internal viscosity (Clenister F K, et al., (2002) *Blood,* 99(3):1060-1063) and (Nash G B, et al., (1989) *Blood*. 74(2):855-861). As the parasite matures, the discoid iRBCs become more spherical with a reduction in surface area to volume ratio leading to reduced cell deformability (Nash G B, et al., (1989) *Blood*. 74(2):855-861) and (Herricks T, et al., (2009) *Cellular Microbiology*. 11(9):1340-1353). Also, release of parasitic proteins stiffens the iRBCs membrane by cross-linking and stabilising the spectrin network in the membrane, thus making it less flexible (Cranston H A, et al. (1984) *Science*. 223(4634): 400-403). Recent studies report that the membrane stiffness of late trophozoite and schizont stages iRBCs further increases at febrile temperature, speculating its role in vascular obstruction in microcirculation (Marinkovic M, et al. (2009) *American Journal of Physiology-Cell Physiology*. 296(1):C59-C64). The RBC deformability (and the lack thereof in iRBCs) has significant physiological relevance. Normal RBCs are highly deformable allowing them to undergo shape deformation when they pass through small capillaries (Sutton N, et al., (1997) *Microvascular Research,* 53(3):272-281), escape clearance by spleen (Safeukui I, et al. (2008) *Blood*. 122(6):2520-2528) and also induce lateral migration at low Reynolds number (Coupier G, et al., (2008) *Physics of Fluids*. 20(11):4). A decrease in iRBC deformability could lead to several important patho-physiological outcomes. For example, Shevkoplyas et al., studied the flow of glutaraldehyde-treated RBCs (with reduced deformability) in a microfluidic device mimicking a microvascular network (Shevkoplyas S S, et al., (2006) *Lab on a Chip*. 6(7):914-920), and showed a decrease in blood flow velocity through the network with increasing RBCs stiffness, resulting in channel clogging and heterogeneous distribution of hematocrit. Recent studies have also shown that stiffened RBCs also affect the thickness of the cell free layer in a stenosed microchannel (Fujiwara H, et al. (2009) *Journal of Biomechanics*. 42(7):838-843), and iRBCs, especially the late-stage trophozoites and schizonts, in vivo mimic the multistep leukocytes recruitment (rolling and subsequent adhesion) on the endothelium (Ho M, et al., (2000) *Journal of Experimental Medicien*. 192(8):1205-1211). Indeed, cytoadherence in the microvasculature helps the iRBCs to evade clearance by spleen which recognizes their loss in deformability. The unique slit-like architecture of the spleen requires RBCs to deform considerably in the narrow inter-endothelial slits in the venous sinuses (Safeukui I, et al. (2008) *Blood*. 122(6):2520-2528). Stiffer iRBCs will be retained upstream in the spleen and undergo "pitting" (mechanically extracting the parasites from the iRBCs via mechanical extrusion) which effectively removes the iRBCs from the circulation, decreasing the parasitic load.

While flow cytometry has been firmly established as a technique to sort cells based on cell surface markers, as shown herein, cell deformability provides an independent yet physiologically meaningful metric to purify/enrich cells. Various techniques have been applied to the separation of cells based on deformability (Xiaomi T et al., (1995) *Journal of Chromatography B: Biomedical Sciences and Applications*. 674(1):39-47) and (Lincoln B, et al. (2004) *Cytometry Part A*. 59A(2):203-209). However, most of these technique operate in batch-flow mode (Xiaomi T et al., (1995) *Journal* of *Chromatography B: Biomedical Sciences and Applications.* 674(1):39-47), resulting in low throughput and the inability to collect cells of different deformability separately (Lincoln B, et al. (2004) *Cytometry Part A.* 59A(2):203-209).

In another aspect, the microfluidic device can be used to detect, separate, and/or isolate circulating tumor cells. Cancer metastasis, mortal consequence of tumorigenesis, accounts for ~90% of all cancer related deaths. Detection of circulating tumor cells (CTCs) which are primarily responsible for metastasis can provide valuable insights associated with disease stage and cancer progression. Their enumeration is also used for clinical evaluations and monitoring of therapeutic treatment response. As CTCs are extremely rare, comprising of as few as one cell per $10^9$ hematologic cells, with highly heterogeneous morphologies and molecular signatures, their isolation from blood has been a technical challenge.

Thus, in one aspect, the invention is also directed to a method of detecting one or more circulating tumor cells in a sample of an individual. The method includes introducing the sample into at least one inlet of a microfluidic device comprising one or more spiral channels wherein each channel has a length and a cross-section of a height and a width defining an aspect ratio adapted to isolate circulating tumor cells along portions of the cross-section of the channel based on cell size, wherein the circulating tumor cells flow along the radially innermost portion of the channel to a first outlet and other cells in the sample flow along another portion of the channel to a second outlet. The method can further include collecting circulating tumor cells from the first outlet, as well as analyzing the circulating tumor cells to assess effectiveness of a therapeutic treatment. The sample can be a blood sample.

A high-throughput cell separation technique for sorting circulating tumor cells (CTCs) from blood using microfluidics is described herein. In one aspect, the design consists of low aspect ratio spirally shaped microchannels fabricated in polydimethylsiloxane (PDMS). The separation relies on the interplay between the inertial lift forces, due to the large cell size, and the Dean drag force, due to the spiral geometry, to equilibrate cells in distinct positions within the microchannel cross-section. By designing an appropriate bifurcated outlet, the cells can then be collected separately based on their size. This technique was applied to separate CTCs which are larger in size, typically ~20 µm in diameter, from blood cells (RBC ~8 µm, white blood cells (WBC) ~10-15 µm) for early cancer detection and monitoring treatment efficiency.

Cells flowing in spiral microchannels are subjected to a combination of inertial lift forces along with the centrifugal acceleration induced Dean drag force. The inertial lift forces, which vary with the fourth power of the cell size, are responsible in focusing the cells at distinct multiple equilibrium positions within the microchannel cross-section. Adding a component of Dean drag, by designing spirally shaped microchannels, these multiple equilibrium positions can be reduced to just one near the inner microchannel wall. As the ratio of lift and Dean drag forces varies for varying cell sizes, the cells can be equilibrated at distinct positions along the microchannel cross-section based on their size, with the largest cells equilibrating closest to the microchannel wall. This results in the evolution of distinct streams of cells which can be independently collected by designing appropriate outlets.

The devices are fabricated in polydimethylsiloxane (PDMS) and bonded to microscopic glass slides (FIGS. 7A and 7B). The microchannel design consists of a 500×100 µm (W×H) microchannel with an expanded 8-equally divided outlet system. The inlet samples consist of diluted whole blood (0.1% hematocrit) spiked with varying CTCs concentration. As the sample flows through the microchannel, normal RBCs, leukocytes and CTCs equilibrate across the microchannel cross-section based on their size. The CTCs, due to the large size (~20 µm), are significantly influenced by the inertial lift force and equilibrate close to the inner channel wall. The RBCs (~8 µm) and leukocytes (10-15 µm), which are smaller than the CTCs, are influenced more by the Dean drag and focus further away from the inner microchannel wall, thus achieving separation. By designing low aspect ratio microchannels, this difference in equilibrium positions can be amplified facilitating the collection of the rare CTCs from outlet 1, as shown in FIG. 8, with the other outlets containing the rest of the blood cells, thus achieving continuous high throughput size-based separation. In another embodiment of this technology, one could use the separation technique to isolate other rare cells including stromal cells from peritoneal fluids, leukemic cells from blood and fetal nucleated red blood cells from maternal blood.

In some embodiments, the aspect ratio of the channel is in a range of between about 1 and about 5, such as about 3.75. In certain embodiments, the method can include separating stem or precursor cells that exist within populations of mixed cell types into functionally distinct subpopulations on the basis of cell diameter. These subpopulations can then be collected from the device and analyzed in terms of unique metabolic function, for example to isolate and enrich a specific subpopulation that may have enhanced capacity to proliferate, differentiate, or respond to particular pharmaceutical agents. In certain embodiments, the width of the channel can be about 500 µm, and the height of the channel can be about 100 µm.

A high throughput size-based cell separation technique for sorting circulating tumor cells (CTCs) from whole blood using spiral microchannel geometry is described herein. The design takes advantage of the inertial lift and viscous drag forces acting on cells of various sizes to achieve differential migration. The dominant inertial forces and the Dean rotation force due to spiral microchannel geometry cause the larger CTCs to focus and occupy a single equilibrium position near the inner microchannel wall. The smaller blood components (RBCs and leukocytes) migrate to the outer half of the channel under the influence of Dean forces, resulting in the formation of two distinct streams which are then collected in two separate outlets. With the ability to process whole blood, the proposed technique takes less than 10 minutes to process 1 mL of whole blood and is able to remove 99% of hematologic cells with 90% CTC recovery in the inner outlet.

Fluid flowing through a curvilinear channel experiences centrifugal acceleration directed radially outward, leading to the formation of two counter-rotating vortices known as Dean vortices, in the top and bottom halves of the channel. The magnitude of these secondary flows is quantified by a dimensionless parameter, the Dean number (De), given by:

$$De = \frac{\rho U_f D_h}{\mu} \sqrt{\frac{D_h}{2R_c}} = Re \sqrt{\frac{D_h}{2R_c}} \quad (1)$$

where $\rho$ is the fluid density, $U_f$ is the average flow velocity, $\mu$ is the viscosity of the fluid, $R_c$ is the radius of curvature of the path of the channel, $D_h$ is the channel hydraulic diameter, and Re is the flow Reynolds number (ratio of inertial to viscous force). Thus, particles flowing in a curvilinear channel experience a drag force due to the presence of these transverse Dean flows, entraining and driving them along the direction of flow within the vortices. This motion translates to the particles moving back and forth along the channel width between the inner and outer walls with increasing downstream distance when visualized from the top or bottom. The velocity with which these cells migrate laterally when flowing in a channel is dependent on the Dean number and can be calculated using:

$$U_{Dean} = 1.8 \times 10^{-4} De^{1.63} \quad (2)$$

The lateral distance traversed by a particle along the Dean vortex can be defined in terms of 'Dean cycle'. For example, a particle which is initially positioned near the microchannel inner wall and migrates to the channel outer wall at a given distance downstream is said to have completed ½ a Dean cycle. Returning back to the original position near the microchannel inner wall completes a full Dean cycle. For a given microchannel length, the particles can thus undergo multiple Dean cycle migration with increasing flow rate (Re) conditions. The length for a complete Dean cycle migration can be calculated as:

$$L_{DC} \sim 2w+h \quad (3)$$

where w is the microchannel width and h is the microchannel height. Consequently, the total microchannel length required for Dean migration is given by:

$$L_C = \frac{U_f}{U_{Dean}} \times L_{DC} \quad (4)$$

Apart from the Dean drag force, larger cells with diameter comparable to the microchannel dimensions also experience appreciable inertial lift forces ($F_L$) (both shear and wall-induced) resulting in their focusing and equilibration. The parabolic velocity profile in Poiseuille flow results in a shear-induced inertial lift force $F_{IL}$ acting on the particles directing them away from the microchannel center towards the channel walls. As these particles move closer to the channel wall, the abrupt presence of the wall disrupts the rotational wake formed around the particles inducing a lift-force ($F_{WL}$) directing them away from the wall, towards the microchannel center. As a result of these two opposing lift forces, the particles equilibrate (focus) around the microchannel periphery at distinct and predictable positions. This effect is dominant for particles with size comparable to microchannel dimensions $a_c/h \sim 0.1$. In microchannels with curvilinear geometry, the interplay between the inertial lift force ($F_L$) and the Dean drag force ($F_D$) reduces the equilibrium positions to just two near the inner channel wall, each within the top and bottom Dean vortex. The two equilibrium positions overlay each other along the microchannel height and are located at the same distance from the microchannel inner wall for a given particle size, i.e., viewed as a single position across the microchannel width.

The work described herein takes advantage of these two phenomena, i.e., Dean migration and inertial focusing, to isolate CTCs from blood. In one aspect, the design comprises a 2-inlet 2-outlet spiral microchannel with a total length of ~10 cm. The microchannel width is about 500 μm and the height is about 140 μm. As shown in FIGS. 15A and 15B, the channel dimensions are selected such that the larger CTCs undergo inertial focusing, while the migration of the smaller hematologic cells (RBCs and leukocytes) is affected by the Dean drag (i.e., only the CTCs satisfy the $a_c/h \sim 0.1$ ratio). At the inlet, whole blood sample is pumped into the inner inlet and sheath fluid (e.g., 1×PBS) through the outer inlet of a spiral microchannel (FIG. 14). Sheath fluid can be used to pinch the whole blood at the inlet, to confine the whole blood sample to a narrow region across the channel width, so that all the cells start to migrate from approximately the same location. During testing, under the influence of the Dean drag forces, the small cells initiate migration along the Dean vortex and move towards the channel outer wall. The strong inertial lift force experienced by the CTCs prevent them from migrating under the influence of Dean drag and cause them to focus and occupy the two equilibrium positions near the microchannel inner wall. On the other hand, since the RBCs and leukocytes are not influenced by the inertial forces, these cells continue to circulate along the Dean vortex. By calculating the appropriate flow rate ensuring that the cells undergo half Dean cycle migration, at the outlet, the CTCs focus near the channel inner walls while the RBCs and leukocytes are transposed to the outer half of the channel. Thus, the CTCs can be isolated and collected at the inner outlet while the other blood cells are collected at the outer outlet (FIG. 14). The advantage of using this technique is its ability to process very high hematocrit samples (whole blood) thus reducing sample preparatory steps and decreasing the analysis time significantly. Using this technique, 1 mL of whole blood can be processed in under 10 minutes.

In another aspect, the method of detecting circulating tumor cells in a sample of an individual includes introducing the sample into at least one inlet of a microfluidic device comprising one or more linear channel wherein each channel has a length and a cross-section of a height and a width defining an aspect ratio adapted to isolate circulating tumor cells along at least one portion of the cross-section of the channel based on cell size, wherein circulating tumor cells flow along the first portion of the channel to a first outlet and other cells in the sample flow along a second portion of the channel to a second outlet. The method can further include collecting circulating tumor cells from the first outlet, and analyzing the circulating tumor cells to assess effectiveness of a therapeutic treatment. The sample can be a blood sample. In some embodiments, the aspect ratio of the channel can be in a range of between about 2 and about 10. In some other embodiments, the aspect ratio of the channel can be in a range of between about 3 and about 5. The width of the channel at the end distal from the inlet can be on the order of the cells to be isolated, that is, the width of the channel at the end distal from the inlet can be about the same size as the size of the cells to be isolated. In some embodiments, the width of the channel can be about 20 μm. The microfluidic device can further include an expansion region at the end of the channel distal from the inlet for improved visualization. In some embodiments, the microfluidic device can further include at least one cell focusing region having a cross-section adapted to cause all cells to migrate to and move along the longer channel dimension.

Figure 16:
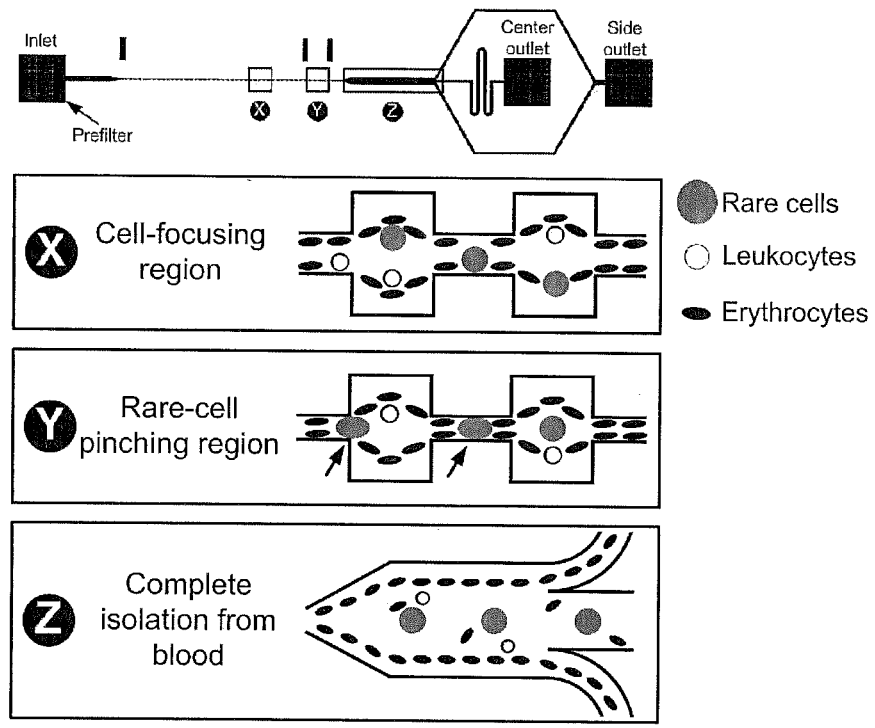
FIG. 16 is a schematic illustration of the microfluidic device for rare-cell isolation from blood. The microchannel design consists of high aspect ratio rectangular microchannel patterned with a contraction-expansion array. In the cell-focusing region, under the influence of shear modulated inertial lift forces all the cells equilibrate efficiently along the channel side walls. Flowing through the rare-cell pinching region, the center of mass of the larger cells are aligned along the channel center while the smaller hematologic cells remain focused along the channel sidewall. Designing bifurcating outlets allows for the collection of the larger rare-cells at the center outlet while the remaining hematologic cells are removed from the side outlet.

Described herein is the application of shear-modulated inertial microfluidics to isolate CTCs from blood. FIG. 16 presents a schematic illustration of the developed micro fluidic device. The device enables efficient separation of rare-cells from peripheral blood by eliminating most or all the erythrocytes, which make up for >99% of all hematologic cells, in a single step. In one aspect, the design consists of a single inlet high aspect ratio rectangular micro channel patterned with a contraction-expansion array. The widths of the contraction and expansion regions were about 20 μm and 60 μm respectively and their lengths were about 100 μm. The channel comprises about 75 subunits of contraction-expansion regions with a total length of about 1.5 cm (a pair of contraction and expansion region makes up one subunit). The outlet opens into an about 300 μm wide section for enhanced visualization and is equally divided into three about 100 μm wide bifurcating arms, two side outlets and a central outlet arm. The target cells are collected in the centre outlet while all other blood components are removed from the side outlets. As an application of this novel technique, demonstrated herein is the separation of rare CTCs from blood with high efficiency (>80% CTC recovery) and throughput (400 μL/min flowrate), permitting the processing of $10^8$ cells/min using a single channel. The channel design allows for easy parallelization with the ability to process milliliters of clinical blood samples within minutes. The device can be customized for isolating other rare-cells from blood including peripheral blood leukocytes and fetal nucleated red blood cells (Vona, G., et al., *American Journal of Pathology*, 2002. 160(1): p. 51).

Inertial lift forces based cell focusing within channels (e.g., microchannels) is fast leading to the development of novel, high-throughput physical cell separation techniques (Bhagat, A. A. S., et al., *Medical and Biological Engineering and Computing*, 2010; Di Carlo, D., *Lab on a chip*, 2009. 9(21): p. 3038). The developed biochip exercises these inertial lift forces for the successful isolation of CTCs from other peripheral blood cells. The high aspect ratio microchannel section can be divided into two regions: (i) cell focusing region and (ii) rare-cell pinching region (FIG. 16). In the cell focusing region (first 70 subunits), under the influence of shear-modulated inertial lift forces, all the cells migrate and equilibrate along the longer channel sidewalls (Bhagat, A. A. S., et al., *Physics of Fluids*, 2008. 20: p. 101702). Neutrally buoyant particles/cells suspended in a fluid flowing through a microchannel are typically subjected to both viscous drag and inertial lift forces. The parabolic laminar velocity profile in plane Poiseuille flows produce a shear-induced inertial lift force resulting in particle migration away from the channel center towards the microchannel walls (Asmolov, E. S., *Journal of Fluid Mechanics*, 1999. 381: p. 63-87). As particles migrate closer to the channel walls, the asymmetric wake induced around particles generates a wall-induced lift force driving these particles away from the walls (Zeng, L., et al., *Journal of Fluid Mechanics*, 2005. 536: p. 1-25). These two opposing lift forces balance out each other, resulting in the equilibration of the uniformly dispersed particles into a narrow band around the microchannel periphery (Matas, J. P., et al., *Oil & Gas Science and Technology*, 2004. 59(1): p. 59-70; Segre, G. et al., *Nature*, 1961. 189: p. 209-210; Segre, G. et al., *J. Fluid Mech*, 1962. 14: p. 115-136; Matas, J. P., et al., *Journal of Fluid Mechanics*, 2004. 515: p. 171-195). These inertial forces are commonly neglected in microfludics based flows, arguably due to the low channel Reynolds number (as a result of the small channel dimensions and low flow rates). However, when particles/cells size is comparable to channel dimensions, these inertial lift forces are significant and lead to the lateral migration of particles across flow streamlines.

For cells to focus in finite channel length for practical microfluidic applications, equilibration occurs for $a_c/D_h \geq 0.07$, where $a_c$ is the cell diameter and $D_h$ is the microchannel hydraulic diameter (Bhagat, A. A. S., et al., *Physics of Fluids*, 2008. 20: p. 101702; Bhagat, A. A. S., et al., *Lab on a chip*, 2008. 8(11): p. 1906-1914; Hampton, R. E., et al., *Journal of Rheology*, 1997. 41: p. 621; Di Carlo, D., et al., *Proceedings of the National Academy of Sciences*, 2007. 104(48): p. 18892). In square microchannels, at low Reynolds number flows (Re<100), eight stable equilibrium positions exist due to the uniform shear gradient on all four sides (Bhagat, A. A. S., et al., *Physics of Fluids*, 2008. 20: p. 101702; Chun, B. et al., *Physics of Fluids*, 2006. 18: p. 031704; Bhagat, A A S., et al., *Microfluidics and Nanofluidics*, 2009. 7(2): p. 217-226). Recent reports have demonstrated that in high aspect ratio rectangular microchannels, the shear rate modulation results in preferential focusing along the longer microchannel dimension (height in this case) (Bhagat, A. A. S., et al., *Physics of Fluids*, 2008. 20: p. 101702; Bhagat, A A S., et al., *Microfluidics and Nanofluidics*, 2009. 7(2): p. 217-226). As the inertial lift force scales as $F_L \propto G^2$ (where G is the shear rate along the channel), high aspect ratio (AR, ratio of channel height to width) rectangular microchannel cross-sections yields a higher shear rate along the channel width ($\propto AR^2$), driving cellular equilibration along the microchannel height. Thus, the dispersed cells at the inlet migrate and align into two streams near the channel sidewalls, creating a cell-free central region. As shown herein, this phenomenon was taken advantage of to focus all the peripheral blood cells along the channels walls for downstream removal. The terms "equilibration" and "focusing" are used interchangeably herein and imply the migration of the cells to the final stationary positions along the longer microchannel sidewalls.

The microfluidic device can also comprise a rare-cell pinching region (e.g., last 5 contraction-expansion subunits) prior to the channel outlet, used for the successful isolation of rare-cells from other hematologic cells (FIG. 16). The contraction width in this pinching region—or pinching width—is designed to be comparable to (i.e., on the order of) the CTCs diameter, such that the center of inertia of these larger cells aligns along the axial centre of the microchannel. Thus, at the outlet, the erythrocytes and PBL remain focused along the channel sidewalls, while the larger CTCs are discharged along the channel axial center, allowing the centre outlet to collect all the rare-cells while >99% of the hematologic cells are removed from the side outlets.

In high aspect ratio devices, the width of the microchannel is an important dimension regulating cell focusing. Herein, this dimension corresponds to the width of the contraction region and was about 20 μm. Ideally, just a straight microchannel (without a contraction-expansion array) is sufficient for efficient cell equilibration along the channel sidewalls (Bhagat, A. A. S., et al., *Physics of Fluids*, 2008. 20: p. 101702; Bhagat, A A S., et al., *Microfluidics and Nanofluidics*, 2009. 7(2): p. 217-226). However, the reasons to include an expansion region at regular intervals are two-fold. First, as these channels are fabricated in PDMS polymer using a double molding process (see Methods Section below), relief structures with aspect ratio >2 are highly susceptible to deformation and distortion (Delamarche, E., et al., *Advanced Materials*, 1997. 9(9): p. 741-746; Xia, Y. et al., *Annual Review of Materials Science*, 1998. 28(1): p. 153-184). About 60 μm wide expansion regions provides greater structural stability for the microchannels, enabling fabrication of features with aspect ratios as high as about 7.5. Second, the expansion regions also help to reduce the pressure drop across the microchannel length, permitting the testing of high flows without device failure (Re>100).

In another aspect, the microfluidic device can be used in a method of isolating one or more synchronized cells from an asynchronous cell mixture. The method includes introducing an asynchronous cell mixture into at least one inlet of a microfluidic device comprising one or more spiral channels wherein each channel has a length and a cross-section of a height and a width defining an aspect ratio adapted to isolate synchronized cells along portions of the cross-section of the channel based on cell size, wherein larger synchronized cells flow along the radially innermost portion of the channel to a first outlet and smaller synchronized cells flow along other portions of the channel to at least one other outlet.

The cell cycle consists of orderly sequential events by which a cell duplicates its contents and then divides into two daughter cells. In eukaryotic cells, these distinct events leading to proper cell division can be divided into four sequential phases: G1 (gap), S (DNA synthesis), G2 (gap) and M (mitosis). As a cell progresses through the cell cycle, it duplicates its chromosomes during S phase and segregates the chromosomes in M phase. In order to maintain long term size homeostasis, the cell must on average double in size before it divides. The G1 and G2 gap phases provide time for synthesis of new macromolecules and various organelles and allow the cell to monitor its external environment to ensure that the conditions are suitable for entry into S and M phases respectively. Following mitosis, cells enter a temporary state of quiescence, the G0 phase, before re-entering the cell cycle.

Cell cycle synchronization is essential for studying cellular properties and biological processes, and for elucidating genetic regulatory mechanisms and events involved in each phase prior to cell division. A synchronized culture is one in which cells reside in a particular phase of the cell cycle and exhibit similar physical and biochemical properties such as size and DNA content. The cells then pass through the cell cycle as a relatively uniform group in the same phases at subsequent time points. Studies with cancer cells have revealed the phenotype and distribution of key oncogenes which are implicated in specific cell cycle checkpoints. Cancer therapeutics have extensively depended on the capability to synchronize tumor cell samples, because anticancer drugs are known to target cells in different phases of the cell cycle. The use of highly synchronized population of cells has also greatly facilitated the development of a variety of biological systems and utility. In stem cell therapies, wherein nuclear transfer is required for the production of cells and tissues that match the patient's immunologic profile, cell cycle synchronization is critical to the success of the technology, as stem cells in the G0/G1 phase impart higher nuclear transfer efficiency. Thus, there is a need to develop efficient techniques to synchronize cells in the various phases of their cell cycle.

A microfluidics based approach to synchronize cells using inertial forces in spiral microchannels is described below. Recently, size based particle separation in microfluidic systems has been developed based on the principles of inertial migration (Bhagat, A. A. S., et al., *Microfluidics and Nanofluidics*, 2009. 7(2): p. 217-226; Di Carlo, D., et al., *Proceedings of the National Academy of Sciences*, 2007. 104 (48): p. 18892). In a spiral shaped microchannel, under Poiseuille flow condition, particles of varying sizes equilibrate at distinct positions along the microchannel cross-section under the influence of inertial lift and Dean drag forces. As described herein, using this principle, several mammalian permanent cell lines, including Chinese Hamster Ovarian Cells (CHO-CD36) and cancer cells (HeLa and KKU-100) were successfully synchronized into populations enriched in G0/G1 (>85%), S and G2/M phase cells. The separation principle exploits the relationship between cell volume (and thus diameter or, more generically "size") and its phase in the cell cycle. Also demonstrated herein is the use of this technique for synchronizing primary cell line-bone marrow-derived human mesenchymal stem cells (hMSCs). The results indicate that the G0/G1 to G2/M ratio of about 2.8:1 of the asynchronous sample is enriched to about 15.7:1. Similarly, about a 4× enrichment in the G2/M population is achieved post synchronization. These results are comparable with those reported using other microfluidic systems (Kim, U., et al., *Proceedings of the National Academy of Sciences*, 2007. 104(52): p. 20708; Thevoz, P., et al., *Analytical chemistry*, 2010. 82: p. 3094-3098; Choi, S., et al., *Analytical chemistry*, 2009. 81(5): p. 1964-1968; Migita, S., et al., *Analytical Methods*, 2010. 2: p. 657-660), although with significantly increased throughput allowing one to synchronize large number of cells (~15×10$^6$/hr) with high viability (~95%). It is believed that the passive operating principle coupled with the microchannel design of this device enables diverse applications in the biological studies of many different primary cell types.

As known to those of skill in the art, "asynchronous cells" are a mixture of cells which are in a variety of phases, e.g., G0/G1, S, and G2/M. As used herein, "synchronized cells" refers to cells in the same cycle of the cell phase. The asynchronous cell mixture can be a suspension of mammalian cancer cells or a suspension of mesenchymal stem cells, a tissue, or a combination thereof. The method can further include collecting synchronized cells from the first outlet. In some embodiments, the aspect ratio of the channel can be in a range of between about 1 and about 5. In certain embodiments, the width of the channel can be about 500 µm, and the height of the channel can be about 140 µm.

The methods described herein can further comprise collecting (isolating) the targeted cells from the device for further analysis, e.g., for fluorescence activated cell sorting, etc.

As will be appreciated by those of skill in the art, the methods can also further comprise enriching the target cells. For example, for a device having multiple outlets, the ratio of the outlet dimensions can be designed to enhance separation and/or enrichment. For example, using a device with 3 outlets as an example, the ratio of the dimensions can be 1:2:1, 1:3:1, 1:4:1, 1:5:1, 1:6:1, 1:7:1, 1:8:1, 1:9:1, 1:10:1, and the like.

Enrichment of the targeted cells can reach, for example, about a 2-fold, about a 3-fold, or about a 4-fold enrichment.

EXEMPLIFICATION

Example 1

Deformability Based Sorting for Cell Separation and Isolation

Materials and Methods
Malaria Culture

*P. falciparum* 3D7 strain was used in this study. Parasites were cultured in RPMI medium 1640 (Invitrogen, USA) supplemented with 0.3 g of L-glutamine, 5 g of AlbuMAX II (Invitrogen, USA), 2 g NaHCO$_3$, and 0.05 g of hypoxanthine (Sigma-Aldrich, USA) dissolved in 1 ml of 1 M NaOH, together with 1 ml of 10 mg/ml of Gentamicin (Invitrogen, USA). Parasites were synchronized at ring stage using 2.5% sorbitol to maintain a synchronous culture. Cultures were stored at 37° C. after gassing with a 5% CO$_2$, 3% O$_2$ and 92% N$_2$ gas mixture and their hematocrit maintained at 2.5%. Cells were harvested at the ring stage, late trophozoite and schizont stage. Whole blood for parasite culture was obtained from healthy donors and was spun down to separate the RBCs. The RBC pellet was treated with CPDA for 3 days before being washed three times with RPMI 1640 and stored for use.

Sample Preparation

The blood sample was washed three times with washing buffer containing 1× phosphate buffer solution (PBS), 2 mM ethylenediaminetetraacetic acid (EDTA) and 1% v/v bovine serum albumin (BSA) prior to running the experiment. Fluorescently labeled microbeads of 3 μm diameter (Fluoresbrite® Microspheres, Polysciences Inc, Singapore) were added (0.01% volume fraction) to the blood and resuspended in sample buffer containing 1×PBS, 2 mM EDTA, 1% BSA, and 3.5 w/v % dextran 40 (AppliChem Asia, Singapore). The dextran provided the effective viscosity of normal plasma and helped to prevent sedimentation and formation of rouleaux during the experiment (Yeh C et al., (1994) 66(5): 1706-1716). The iRBCs (0.01% parasitemia) were stained with 4',6-diamidino-2-phenylindole (DAPI) (Sigma Aldrich, USA) for visualization and quantification. Final blood suspension was then adjusted to various hematocrit (1%, 10% and 40%) with sample buffer accordingly.

Device Characterization

The devices were fabricated in polydimethylsiloxane (PDMS) (Sylgard 184, Dow Corning, USA) using standard microfabrication soft-lithographic techniques (McDonald J C et al., (2002). *Accounts of Chemical Research.* 35(7): 491-499). To characterize the microfluidic devices, cell sample was filled in a 1 cc syringe and pumped into the microfluidic devices using a syringe pump (Fusion 400, Chemyx Inc., USA) driven at varying flow rates. Flow was experimentally observed using an inverted epi-fluorescence microscope (Olympus IX81, Olympus Inc., USA) equipped with a 12-bit EMCCD camera (iXonEM+885, Andor Technology, USA). During testing, high speed images of the channel were captured at the outlet using Metamorph® software (Molecular Devices, USA).

To quantify the separation efficiency, the dispersion of the fluorescently labeled microbeads and iRBCs was measured from the images taken at the microchannel outlet. Microbeads and iRBCs dispersion were measured by dividing the 100 μm wide outlet microchannel into 10 equal bins of 10 μm each and counting the number of beads/iRBCs passing through each bin (Bhagat A A S et al., (2008) *Journal of Micromechanics and Microengineering.* 18(8): 9). The count was then plotted to show the distribution of the beads/iRBCs across the channel width. Filtration efficiency was determined by normalizing the beads/iRBCs count measured at the side outlet to the total outlet count. For complete filtration, all the beads/iRBCs are expected to migrate to the two channel sidewalls and be effectively filtered from the two side outlets. The separation efficiency was further verified by performing fluorescence activated cell sorting (FACS) analysis using BD™ LSR II flow cytometer (BD Biosciences, USA) on the collected outlet samples.

Microchannel Design

Figure 1B:
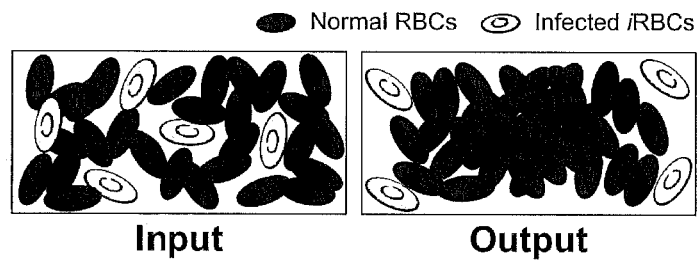
Figure 1B:
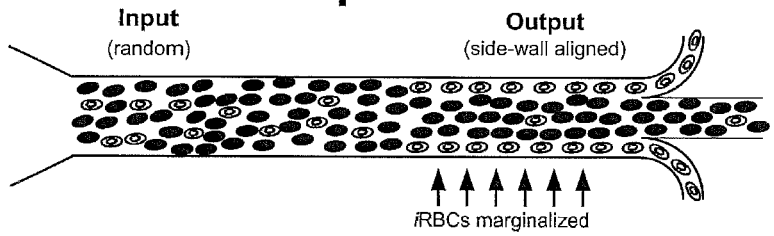

This microchannel design was a 3 cm long, 15×10 μm (W×H) microchannel with an expanded asymmetrical 3-outlet system. Microchannels began with a 100 μm wide segment at the input that constricted to 15 μm; at the output the microchannel opened into a 100 μm wide section to enhance visualization. Before testing with iRBCs infected blood, the filtration principle was corroborated using hard polystyrene 3 μm beads suspended in whole blood. The 3 μm beads were chosen as they are similar in size to the parasites found in late stage iRBCs and are thus representative of the actual iRBCs behavior. The sample consists of whole blood (40-45% hematocrit) spiked with 0.05-0.1% beads or iRBCs of different stages. As the blood sample flows through the 15×10 μm microchannel, normal RBCs, which are more deformable than the iRBCs, migrate laterally to the axial centre of the channel, displacing the stiffer iRBCs towards the channel wall. By designing low aspect ratio microchannels, iRBCs are allowed to marginalize only along the channel width and thus align near each sidewall. The iRBCs are then filtered using the asymmetrical 3-outlet system, thus achieving continuous high throughput deformability-based filtration. FIG. 1 shows a schematic illustration of the developed microfluidic design.

Results and Discussion

Figure 2A:
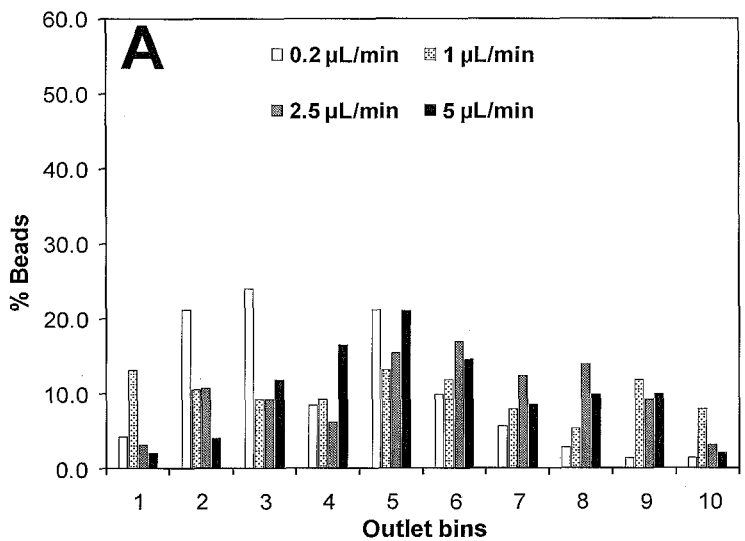
FIGS. 2A-2C are histograms showing the normalized 3 μm beads distribution at the microchannel outlet for varying flow rates in 2(A) 1% hematocrit, 2(B) 10% hematocrit and 2C 40% hematocrit samples.
Figure 2B:
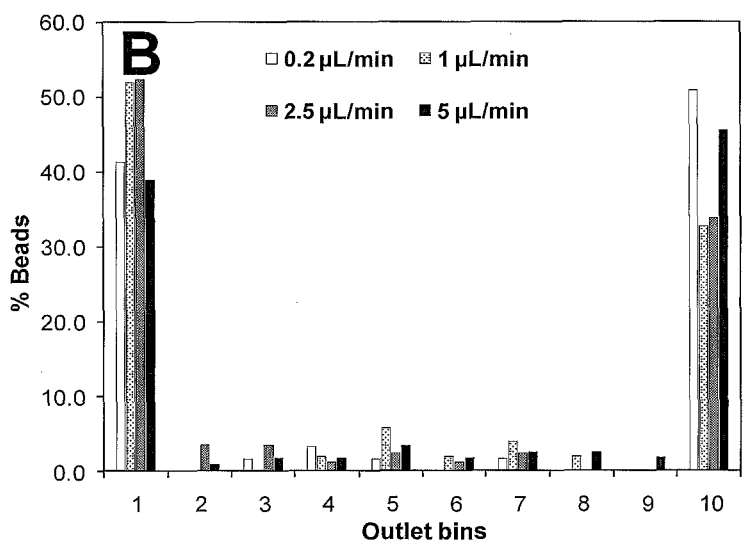
Figure 2C:
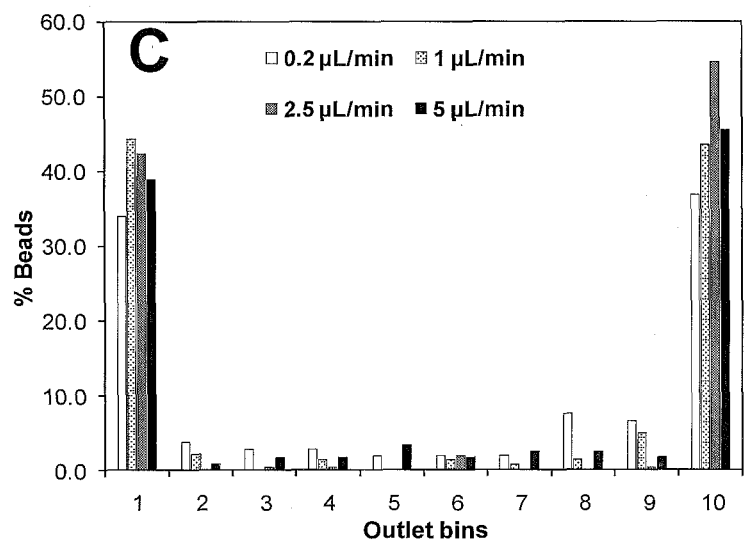
Figure 3A:
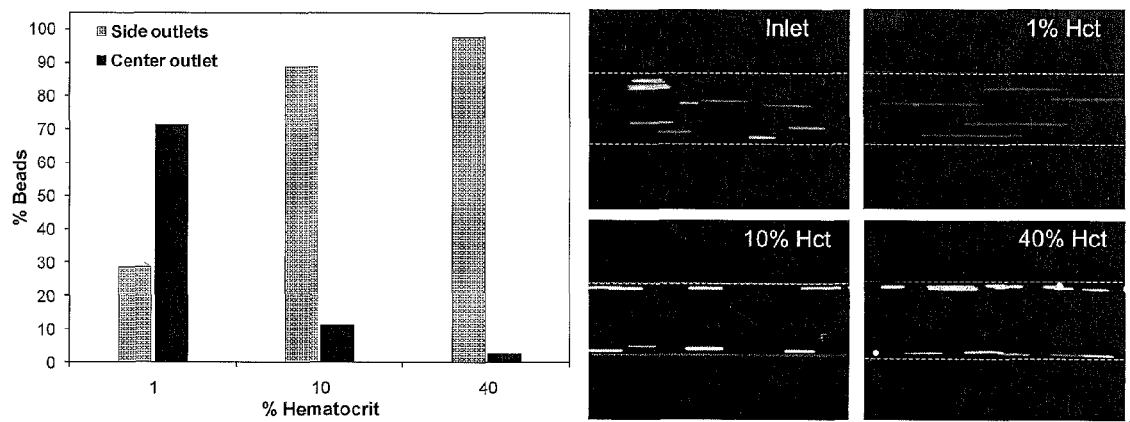
FIGS. 3A and 3B are graphs of: 3A Filtration efficiency of 3 μm beads at the side outlets for varying sample hematocrit at 5 μL/min flow; 3B Filtration efficiency of 3 μm beads at the side outlets at varying flow rates in 40% hematocrit sample. Also, shown in the figure are fluorescent images indicating the beads distribution across the channel cross-section at the outlet (white dotted lines indicate the approximate channel wall boundaries).

To validate the phenomenon of deformability-based lateral displacement in concentrated blood flow, rigid polystyrene microbeads of 6 μm diameter, which are approximately of the same dimension as RBCs, were initially tested in blood suspension of 10-40% hematocrit. By the time the flow reached the outlet, all beads were aligned near the two sidewalls of the microchannels, confirming margination. The experiments were then repeated with smaller 3 μm fluorescently labeled polystyrene beads, because of the similarity in size with the parasites (3 to 5 μm) found in late stages iRBCs. As the stiff parasites are mainly responsible for the loss of deformability in infected cells (Nash G B, et al., (1989) *Blood.* 74(2):855-861), 3 μm beads give a good representation of iRBCs flow behavior. The beads were added into blood suspensions of 1%, 10% and 40% hematocrit and pumped through the device at varying flow rates. The separation efficiency was quantified by counting the beads passing through each bin location. For consistency, a total of 200 beads were counted for each experiment. FIGS. 2A-2C plot the beads distribution across the microchannel width for varying flow rates. At low hematocrit (1% Hct), the beads and RBCs remained uniformly dispersed across the channel width, indicating negligible axial migration and margination. Increasing the hematocrit to 10% and 40%, results in the formation of a well developed RBC dominated core at the microchannel center. Due to strong interactions between the beads and RBCs, almost all the beads (>90%) were displaced towards the channel sidewalls (bins 1 and 10 in FIGS. 2B-2C). These results are in accordance to those reported by others, suggesting the role of high hematocrit for cell margination (Jain A et al., (2009) *PLoS ONE.* 4(9): e7104). FIG. 3A presents the 3 μm beads distribution measured at the side outlets and the center outlet arm for varying hematocrit samples. All experiments were conducted at a fixed flow rate of 5 μL/min. At 1% hematocrit, the centre outlet had approximately twice as many beads than the side outlets. This is attributed to the higher velocity at the microchannel center (Poiseuille flow), resulting in more beads passing though the center in a given time period. However, at higher hematocrit (10% and 40%), almost all the beads (~90%) were displaced to the channel sidewalls and collected by the side outlets. The filtration efficiency also increased from 89% to 97% as the hematocrit was increased from 10% to 40%, an indication of increased margination (Zhao R, et al. (2008) *Annals of Biomedical Engineering.* 36(7):1130-1141).

Figure 3B:
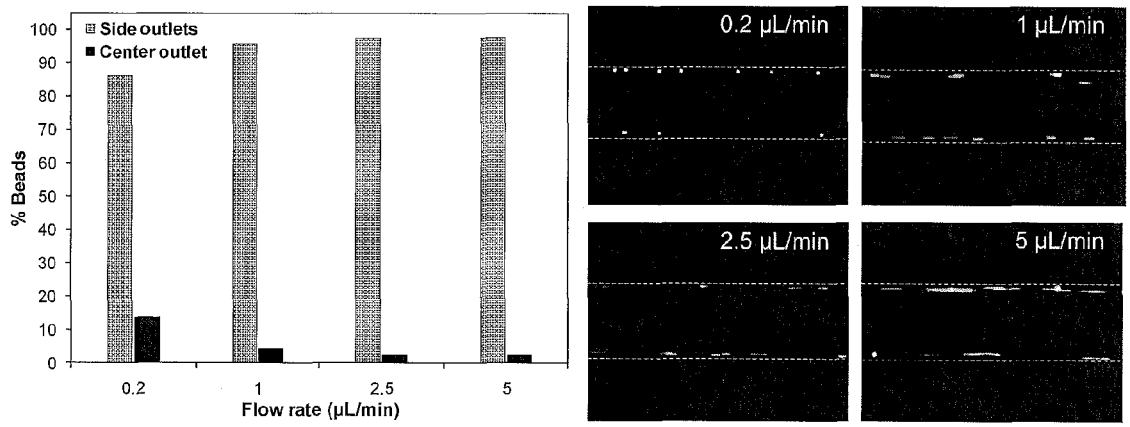

A high hematocrit sample results in improved lateral displacement of beads in our microchannel. Next, experiments were conducted to determine the effect of flow rate on separation efficiency. Based on the results presented in FIG. 3A, a 40% hematocrit sample spiked with fluorescently labeled beads was tested at flow rates ranging from 0.2 μL/min to 5 μL/min. FIG. 3B presents the 3 μm beads distribution measured at the side outlets and the center outlet arm for increasing flow rates. The bead margination efficiency remained approximately constant at ~90% at all tested flow conditions, consistent with other recently reported results (Zhao R, et al. (2008) *Annals of Biomedical Engineering.* 36(7):1130-1141). This behavior can be accounted for by the following reasons. At lower flow rates, the rigid beads take longer to traverse the channel length, thus allowing sufficient time for multiple cell interactions for lateral margination. However, when the flow rate is increased, due to higher inertia, the RBCs migrate faster to the axial center of the microchannel, forming a well-defined core. This results in the rigid beads being "pushed" away from the center towards the sidewalls, thus achieving efficient separation even at higher flow rates.

Figure 4A:
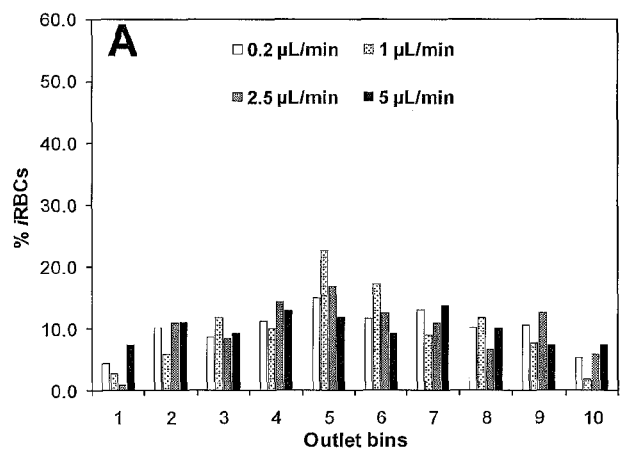
FIGS. 4A and 4B are histograms showing the normalized iRBCs distribution at the microchannel outlet for varying flow rates in 4A 10% hematocrit and 4(B) 40% hematocrit samples. Contrary to the 3 μm bead results, no iRBCs margination is observed at 10% hematocrit. At 40% hematocrit, ~80% iRBCs marginate to the sidewalls for all flow conditions.
Figure 4B:
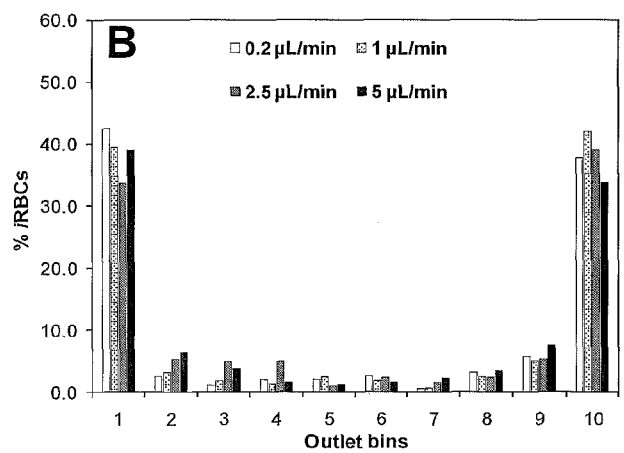

Following the validation of the design principle with the experiments using polystyrene beads, tests with malarial infected iRBCs were next conducted. Based on the results presented in FIGS. 3A and 3B, iRBCs with 10% and 40% hematocrit samples were tested. Initially, all tests were done using late trophozoite/schizont stages iRBCs, as the margination effect would be more prominent due to their increased stiffness when compared with the early stage iRBCs. FIGS. 4A and 4B present the iRBCs distribution results measured at the microchannel outlet for 10% and 40% hematocrit at varying flow conditions. At 10% hematocrit, contrary to the results obtained with the hard polystyrene beads, we see negligible iRBCs marginating towards the side walls. The iRBCs count indicates a parabolic distribution around the channel axial center, consistent with the Poiseuille velocity profile. This indicates that the difference in deformability between the iRBCs and normal RBCs is not sufficient to displace the iRBCs towards the sidewalls with moderate cell-cell interactions.

However, increasing the hematocrit to 40% results in significant iRBCs margination (FIG. 4B). From the figure, ~80% iRBCs were displaced to bins 1 and for all flow conditions, similar to the results obtained with the polystyrene beads. The margination effect was observed at all flow rates tested indicating that the hematocrit is a main factor for iRBCs margination. The higher hematocrit facilitates increased cell-cell interactions displacing the less-deformable iRBCs to the channel sidewalls, thus allowing efficient separation of infected cells, and thus demonstrating the use of cell margination for the separation of less-deformable iRBCs, advocating the application of this technique for diagnosis of other diseases characterized by a change in erythrocyte cell stiffness, such as sickle cell anemia and leukemia.

Figure 5:
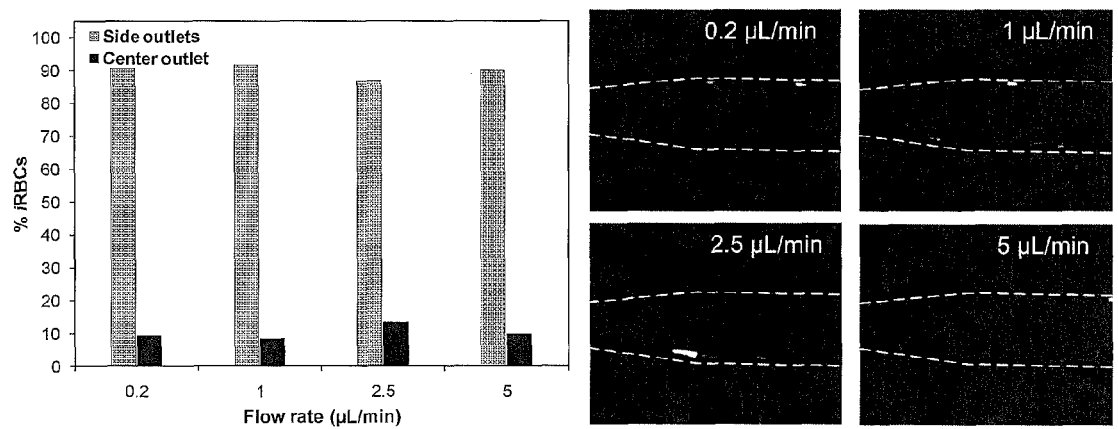
FIG. 5 is a graph of the filtration efficiency of late trophozoite/schizont stage iRBCs at the side outlets at varying flow rates in 40% hematocrit sample. Also, shown in the figure are fluorescent images indicating the DAPI stained iRBCs distribution across the channel cross-section at the outlet (white dotted lines indicate the approximate channel wall boundaries).

FIG. 5 presents the separation efficiency of this iRBCs margination phenomenon for varying flow rates. It is important to note that the technique worked equally well at all tested flow conditions including high flow rates (5 µL/min), an important consideration for high-throughput separation. As expected, the iRBCs separation efficiency was not as high as that measured with hard beads since the iRBCs are still deformable and thus marginalize less efficiently to the sides.

Figure 6A:
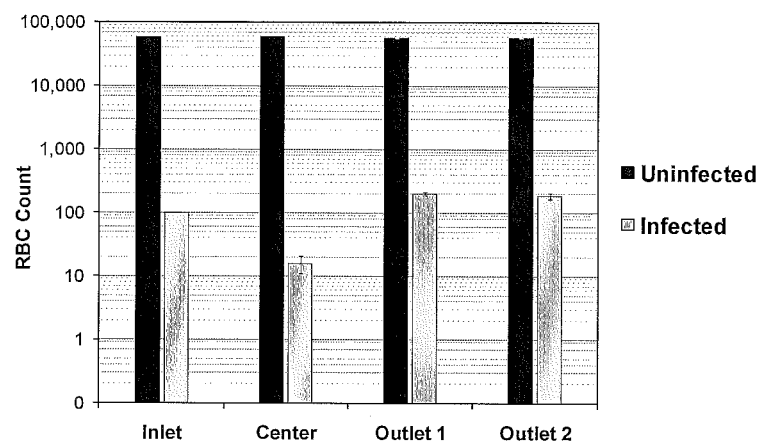
FIGS. 6A and 6B are graphs of flow cytometry (FACS) data indicating concentration of the iRBCs and normal RBCs collected at the three outlets. The plots illustrate the counting results indicating the distribution of iRBCs across the three outlets for 6A late trophozoite/schizont stage and 6B ring stage iRBCs samples. The results indicate a filtration efficiency of >90% for late trophozoite/schizont stage iRBCs and ~75% for early ring stage iRBCs.

Finally, to verify the accuracy of the filtration efficiency, the outlets samples were analyzed using fluorescence activated cell sorting (FACS). Both ring stage and late trophozoite/schizont stage iRBCs at 40% hematocrit blood suspension were pumped through the device at 5 µL/min and the outlets were collected and analyzed using FACS. A total of 500,000 events were recorded giving a more accurate representation of the iRBCs separation efficiency. For experiments with late trophozoite/schizont stages iRBCs, a 92% filtration efficiency was measured between the side and center outlets, consistent with the bin counting data (FIG. 6A). The iRBCs concentration at the side outlets show 2× enrichment compared to the inlet sample, as the side outlets account for 50% volume of the three outlets. However, this number is affected by the non-optimized design of the outlet channels, and can be further improved if the same process can be repeated.

Figure 6B:
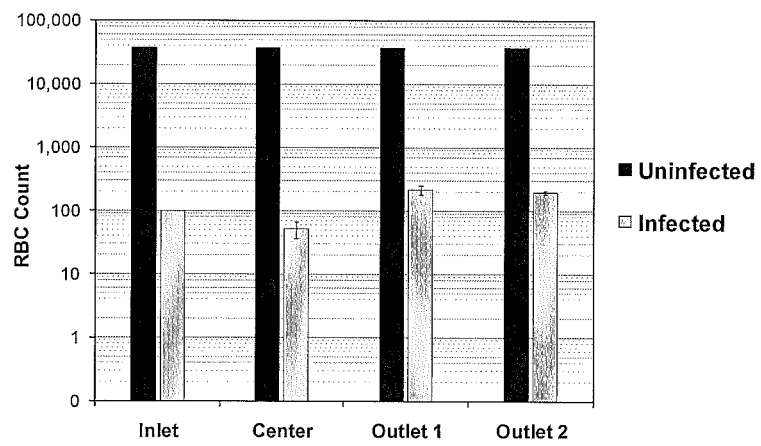

To apply this iRBCs margination for malaria diagnostics, it is important to enrich the ring stage iRBCs. Typically, in malaria-infected patients, late stages (trophozoite/schizont) iRBCs would sequester in the post-capillary venules and only the ring stage iRBCs are observed circulating in the peripheral bloodstream for detection of malaria infection (Demirev P A, et al. (2002) *Analytical Chemistry.* 74(14): 3262-3266) and (Gascoyne P, et al. (2002) *Lab on a Chip* 2(2):70-75). Separation efficiency of the technique for ring stage iRBCs were tested under optimized separation conditions (40% hematocrit, 5 µL/min), and the collected outlets were analyzed using FACS (FIG. 6B). Ring stage iRBCs are only marginally stiffer than uninfected cells due to a reduction in cell surface area to volume ratio and stiffening of the cell membrane (Suresh S, et al. (2005) *Acta Biomaterialia.* 1(1):15-30); (Nash G B, et al., (1989) *Blood.* 74(2):855-861) and (Herricks T, et al., (2009) *Cellular Microbiology.* 11(9): 1340-1353). However, even this subtle difference in deformability can be exploited using this phenomenon of margination for iRBCs filtration. Understandably, the separation efficiency of ring stage iRBCs is lower than that of the late stages iRBCs. Results indicate that the ring stage iRBCs also marginate towards the channel sides, resulting in a separation efficiency of ~80%. Analyzing captured videos, it was seen that the late stage iRBCs get displaced entirely to the sidewalls whereas the early stage iRBCs did not marginate as much. This can be further improved using e.g., longer microchannels, thus allowing the ring stage iRBCs sufficient time to marginate entirely to the sidewalls. Also, by appropriately dividing the outlets (for example using a 1:10:1 width ratio rather than 1:2:1 ratio between the three arms) the developed microfluidic device could also be used as an enrichment tool for malaria diagnosis with improved detection sensitivity at low parasitemia.

Stiffer iRBCs behave like leukocytes and undergo margination towards the side walls. This demonstration provides insights into the hemodynamic effects of iRBCs microcirculation and its pathophysiological significance to cytoadherence. As mentioned earlier, two key morphological changes in iRBCs are the increase in adhesiveness of the iRBC membrane and reduced deformability. These changes are pivotal in severe malaria pathogenesis leading to cytoadherence of iRBCs to various types of host cells. Margination of these iRBCs to the capillary walls also leads to sequestration at the venular blood capillaries, responsible for capillary blockages and comprising the microcirculation (Dondrop A M, et al., (2000) *Parasitology Today.* 16(6): 228-232) and (Cooke B M, et al., (2000) *Parasitology Today.* 16(10):416-420). Ho et al., have shown in vivo that iRBCs cytoadherence to endothelium mimic the multistep leukocytes recruitment such as rolling and adhesion and this process happened in both human post capillary venules and the arteriolar vasculature (Ho M, et al., (2000) *Journal of Experimental Medicine.* 192(8):1205-1211). The results presented illustrate the rigid late trophozoite/schizont stage iRBCs being laterally displaced and flowing at the periphery of the microchannels. This, in vivo, would favor their entrance into the small branching side capillaries resulting in subsequent iRBCs sequestration in the capillary bed. Also tested was iRBCs margination over a wide range of flow conditions (Re=0.01-2.22), similar to physiological arteriole flow (Popel A S et al., (2005) *Annual Review of Fluid Mechanics*. 37: 43-69), further confirming the role of reduced deformability to in vivo sequestration and cytoadherence.

The physiological phenomenon of cell margination was applied to achieve continuous deformability-based filtration of iRBCs in a microfluidic device. The technique offers many distinct advantages over other microfluidic separation methods. First, continuous operating mode enables a high sample throughput (5 μL/min, ~20 million cells/min), enhancing detection sensitivity at low parasitemia (Gascoyne P, et al. (2002) *Lab on a Chip*. 2(2): 70-75; Zimmerman P A, et al., (2006) *American Journal of Tropical Medicine and Hygiene*. 74(4): 568-572). Passive operating principle eliminates the need to integrate an external force field for functionality, making it ideal for outfield settings. As whole blood from patients can be tested directly, sample preparatory steps are not necessary unlike other microscale separation techniques (Zimmerman P A, et al., (2006) *American Journal of Tropical Medicine and Hygiene*. 74(4): 568-572; Karl S, et al. (2008) *Malaria Journal*. 7(1): 66), further reducing processing time and cost. Also, as no special chemicals or antibodies are needed, it helps to solve reagent storage problems which are a major concern for malaria-affected countries that suffer from hot and humid weather and lack refrigeration (Stevens D Y, et al. (2008) *Lab on a Chip*. 8(12): 2038-2045). Finally, the low-cost and disposable nature of the device makes it ideal for on-the-field clinics.

Conclusions

Here, a continuous deformability-based iRBCs filtration method in a microfluidic device based on biomimetic cell margination is introduced. Demonstrated herein is that stiffer iRBCs behave like leukocytes and marginate towards the side walls under physiological conditions. The results indicate that high sample hematocrit (40%) was important for optimal margination, observed over a wide range of flow rates. Tests were conducted with both ring stage and late trophozoite/schizont stage iRBCs mixed with whole blood at a relatively high throughput of 5 μL/min. Filtration efficiency was determined using the individual bin-counting method and FACS analysis. The reported results indicate a high filtration efficiency of ~75% for early ring stage iRBCs and >90% for late trophozoite/schizont stage iRBCs. As whole blood samples can be used directly in this passive microfluidic device, eliminating the need for additional sample modification and preparation, this technique is ideal for on-site testing in resource-poor settings making diagnosis faster and more accurate. Finally, as the separation principle is based on deformability differences as an intrinsic biomarker, the device can be readily applied to other blood cells diseases such as sickle cell anemia and leukemia which are also characterized by change in cell stiffness.

Example 2

Cell Cycle Synchronization in Spiral Microfluidics

Materials and Methods
Cell Culture

Mesenchymal stem cells (Lonza, Switzerland) were cultured in low-glucose Dulbecco's modified Eagle's medium (DMEM) (Invitrogen, USA) supplemented with 10% fetal bovine serum (FBS) (Invitrogen, USA) together with 1% penicillin-streptomycin (Invitrogen, USA). The Chinese hamster ovary cells transfected with human CD36, CHO-CD36 (ATCC, USA), were cultured in RPMI 1640 medium (Invitrogen, USA) supplemented with 10% FBS together with 1% penicillin-streptomycin. The cervical cancer cells HeLa (CCL-2™, ATCC, USA) were cultured in low-glucose DMEM supplemented with 10% FBS and 1% penicillin-streptomycin. The cholangiocarcinoma cell line, KKU-100 (received as a gift), were cultured in Ham's F-12 medium containing 10% FBS, 3% HEPES buffer and 1% penicillin-streptomycin. All cultures were maintained at 37° C. in a humidified atmosphere containing 5% (v/v) $CO_2$. The MSCs were seeded at 500 cells/$cm^2$ and cultured in sterile 175 $cm^2$ flasks (Coming) and dissociated after 48 hours with 0.01% trypsin and 5.3 mM EDTA solution to prevent contact inhibition. The CHO-CD36, HeLa and KKU-100 cells were cultured in sterile 25 $cm^2$ flasks (Corning) and sub-cultivated (1:4) three times a week and media was replaced every 48 h. Sub-confluent monolayers were dissociated with 0.01% trypsin and 5.3 mM EDTA solution.

Prior to testing, the asynchronous cells were diluted to 100,000 cells/mL in buffer containing 1× phosphate buffered saline (PBS), 2 mM ethylenediaminetetraacetic acid (EDTA) supplemented with 1% bovine serum albumin (BSA) (Miltenyi Biotec, Germany) to prevent agglomeration and adsorption to the microchannel walls. The solution density was adjusted to prevent settling of cells by supplementing with 3.5% w/v Dextran 40 (AppliChem Asia, Singapore).

Mesenchymal Stem Cell Synchronization by Contact Inhibition and Serum Starvation To initiate G1 arrest by contact inhibition, MSCs were seeded at 20,000 cells/$cm^2$ and cultured in DMEM supplemented with 10% FBS for 48 h. For G1 arrest by serum starvation, MSCs were seeded at 500 cells/$cm^2$ and cultured in DMEM without FBS for 48 h. The arrested cells were dissociated with 0.01% trypsin and 5.3 mM EDTA solution before fixing in 70% ethanol for 30 minutes.

Microchannel Fabrication

Figures 9A, 9B:
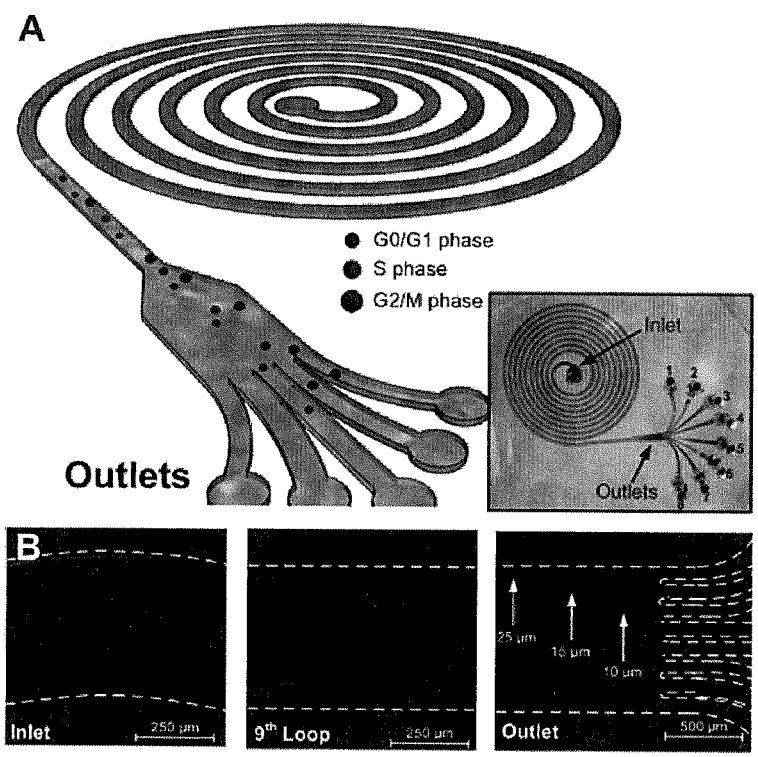

The devices were fabricated in polydimethylsiloxane (PDMS, Sylgard 184, Dow Corning, USA) using standard soft-lithographic techniques (Xia, Y. et al., *Annual Review of Materials Science*, 1998. 28(1): p. 153-184) (FIG. 9A). Briefly, 6" silicon wafers were first patterned and etched using deep reactive ion etching (DRIE) to define the channels on the wafer. Following etching, the patterned silicon wafers were treated with trichloro (1H,1H,2H,2H perfluorooctyl) silane (Sigma Aldrich, USA) for 2 h to facilitate PDMS mold release. Following silanization, PDMS prepolymer mixed at a 10:1 (w/w) ratio with curing agent was poured on the silicon master and cured at 70° C. for 2.5 h. The cured PDMS mold was then peeled from the silicon wafer and used as a master template for subsequent PDMS casting. Next, the PDMS template was silanized for 2 h to aid release of subsequent PDMS molds. Following curing on the final PDMS molds with the desired patterns, holes for inlet and outlets were punched using a 1.5 mm biopsy punch. The PDMS molds were then irreversibly bonded to microscopic glass slides (1"×3"×1 mm; Fisher Scientific Inc., USA) using oxygen plasma treatment (Covance, Femto Science, South Korea).

Device Characterization

Fluorescent polystyrene beads (25 μm-green, 15 μm-blue and 10 μm-red) (ITS Science & Medical, Singapore) were suspended in equal proportions in 1×PBS and 3.5 (w/v) Dextran 40 with 1% BSA at a total concentration of 1.2×$10^5$ beads/mL. To characterize the spiral microfluidic device, the bead mixtures and cell suspensions were filled in a 60 mL syringe and injected into the microchannel using a syringe pump (NE-1000, New Era Syringe Pump Systems Inc., USA) driven at 2.5 mL/min flowrate. Flow was experimentally observed under an inverted epi-fluorescence microscope (Olympus IX81, Olympus Inc., USA) equipped with a 12-bit EMCCD camera (iXon™+885, Andor Technology, USA). Following testing, microscopic images of the cell samples collected from the outlets were captured and the cell size calculated from the photographs using Metamorph® software (Molecular Devices, USA).

Cell Cycle Analysis Using FACS

Flow cytometry analysis using propidium iodide (PI) was performed on the sorted samples to analyze the cellular DNA content (Wersto, R. P., et al., *Cytometry Part B: Clinical Cytometry*, 2001. 46(5): p. 296-306). The sorted synchronized cell samples were washed in 1×PBS and fixed in 70% ethanol for 30 min at 4° C. Cells were then centrifuged at 600 g for 5 min and incubated for 30 min in the staining solution containing 1×PBS, 3.8 mM sodium citrate (Sigma Aldrich, USA), 10 g/ml RNase (i-DNA Biotechnology, Singapore) and 50 g/ml propidium iodide (Sigma Aldrich, USA). The stained cells were then tested for synchronization efficiency by performing FACS analysis using BD™ LSR II flow cytometer (BD Biosciences, USA) and Cyflogic (CyFlo Ltd, Finland) data analysis software.

Results and Discussion

Design Principle

FIG. 9A shows a schematic illustration of the spiral separators. Size-based cell separations using inertial forces in microfluidic systems have gained interest due to their high separation resolution and extremely high throughput. In simple particle-laden tube flows, under Poiseuille flow conditions, balance between the shear-induced and wall-induced lift forces equilibrates the suspended particles in an annular fashion around the tube periphery, the "tubular pinch" effect (Segre, G., *Nature*, 1961. 189: p. 209-210; Segre, G. et al., *Journal of fluid mechanics*, 1962. 14(01): p. 115-135; Matas, J. P., et al., *Journal of fluid mechanics*, 2004. 515: p. 171-195). Chun and Ladd demonstrated that in channels with rectangular cross-sections the lift force ($F_L$) equilibrates the particles at eight distinct positions across the channel cross-section, reflecting the broken symmetry compared to a tube (Chun, B. et al., *Physics of Fluids*, 2006. 18: p. 031704). Numerical calculations by Asomolov show that this lift force is very sensitive to the particle size (d) and varies with its fourth power ($F_L \propto d^4$) (Asmolov, E. S., *Journal of fluid mechanics*, 1999. 381: p. 63-87). Recently, this inertial migration of particles has been employed in microchannel flows for separation of 1.9 μm and 590 nm particles (Bhagat, A. A. S., et al., *Microfluidics and Nanofluidics*, 2009. 7(2): p. 217-226). Studies indicate that for d/D≥0.07, where D is the microchannel diameter, these inertial lift forces are significantly large resulting in particle equilibration within short distances, ideal for microfluidic systems (Bhagat, A. A. S., et al., *Microfluidics and Nanofluidics*, 2009. 7(2): p. 217-226; Di Carlo, D., et al., *Proceedings of the National Academy of Sciences*, 2007. 104 (48): p. 18892; Hampton, R. E., et al., Migration of particles undergoing pressure-driven flow in a circular conduit. *Journal of Rheology*, 1997. 41: p. 621). In low aspect ratio rectangular microchannels, the microchannel diameter D can be approximated to the microchannel height (H) (Bhagat, A. A. S., et al., *Physics of Fluids*, 2008. 20: p. 101702).

In spiral shaped microchannels, the outward directed centrifugal force gives rise to counter rotating vortices, also known as Dean vortices, in the top and bottom half of the microchannel. These secondary Dean vortices exert a drag force on the suspended particles, entraining them within the vortex. The magnitude of this Dean drag force ($F_D$) varies with the particle size and its position within the channel cross-section ($F_D \propto d$). Particles flowing in spiral micro channels are thus subjected to both the inertial lift forces and the Dean drag force. The interplay between the inertial lift force ($F_L$) and the Dean drag force ($F_D$) reduces the eight equilibrium positions to just two near the inner channel wall, each within the top and bottom Dean vortex (Russom, A., et al., *New Journal of Physics*, 2009. 11: p. 075025). The two equilibrium positions overlay each other along the microchannel height and are located at the same distance from the microchannel inner wall for a given particle size, i.e., viewed as a single position across the microchannel width (FIG. 9B). As this focusing position is dependent on both $F_L$ and $F_D$, it varies significantly with the particle size $F_L/F_D \propto d^3$. This implies that particles of different sizes occupy different lateral positions within the microchannel cross-section, with the largest particle being closest to the inner channel wall (Kuntaegowdanahalli, S. S., et al., *Lab on a Chip*, 2009. 9(20): p. 2973-2980). By designing bifurcating outlets, the different size fractions can then be extracted, achieving separation.

Continuous size-based separation using the combined effect of inertial lift forces and the Dean force was applied by Kuntaegowdanahalli et al., for the separation of 10 μm, 15 μm and 20 μm particles in a single pass and for the separation of SH-SY5Y neuroblastoma and C6 rat glioma cells (Kuntaegowdanahalli, S. S., et al., *Lab on a Chip*, 2009. 9(20): p. 2973-2980). Russom et al., further applied this technique to achieve leukocyte enrichment in blood (Russom, A., et al., *New Journal of Physics*, 2009. 11: p. 075025). In this work, we adapted this principle for the synchronization of cells based on their phase in the cell cycle. The device operating principle exploits the relationship between cell volume (and thus their size) and its phase in the cell cycle to synchronize them. As described herein, human mesenchymal stem cells (hMSCs) were size fractionated into synchronized populations of G1/G2, S and G2/M phase cells.

To corroborate the design principle and determine the flow conditions, a mixture of 25 μm, 15 μm and 10 μm sized fluorescently labeled polystyrene beads were tested through the spiral microchannel. The diameters of the beads were chosen to mimic the size range of mammalian cells. The microchannel design consisted of 9-loop spiral geometry with one inlet and eight bifurcating outlets. The microchannel width was fixed at 500 μm and the height was varied to satisfy the d/D>0.07 ratio for the different cell types. FIG. 9B presents superimposed fluorescent images of the microbeads captured at the inlet and outlet of the microchannel at an optimized flowrate of 2.5 mL/min. By the time the flow reaches the outlet, the 25 μm, 15 μm and 10 μm beads are focussed into three distinct streams across the microchannel cross-section and efficiently collected at outlet 1, 2 and 3 respectively.

Synchronization of Permanent Cultures

In an exponentially growing mammalian culture, newborn cells in G1 phase have sizes at the lower end of the size distribution of the culture (Cooper, S., *Cellular and Molecular Life Sciences*, 2003. 60(6): p. 1099-1106). As the cells achieve a critical size through protein and lipid synthesis, the cells initiate a new cell cycle in late G1 phase and synthesize DNA in the S phase. Cell growth continues until mitosis (M phase) where the cell grows to about twice the original size of that in the G0/G1 phase. Correspondingly, cells in the G2/M phase have two copies of DNA.

The synchronization performance of the device was investigated using two cancer cell lines—HeLa and KKU-100 cells. As the mean diameter of the HeLa and KKU-100 cells population was measured as 16.3±2.5 µm and 17.8±2.4 µm respectively, the cells were sorted using a 140 µm high spiral microchannel (satisfying the d/H≥0.07 condition). When the cells are introduced into the microchannel, the asynchronous cells with broad size distribution are separated into distinct trajectories at different lateral positions along the inner half of the microchannel. After sorting, optical microscopic images of the unsorted (control) and sorted cells collected from outlets 1-4 were taken and their diameters recorded and analyzed. The cells were successfully separated on the basis of their size. The biggest cell populations were collected in the outlet closest to the inner microchannel walls (outlet 1) with mean diameters of 19.4±5.6 µm (HeLa) and 24.6±3.0 µm (KKU-100). The smallest HeLa and KKU-100 cell populations were collected in outlet 4 with mean diameters of 13.5±1.5 µm and 16.6±2.4 µm respectively. Similarly, another cell line, CHO-CD36 was also size fractionated using a 200 µm high microchannel to accommodate the larger size distribution (13.3-36.7 µm).

Figure 10A:
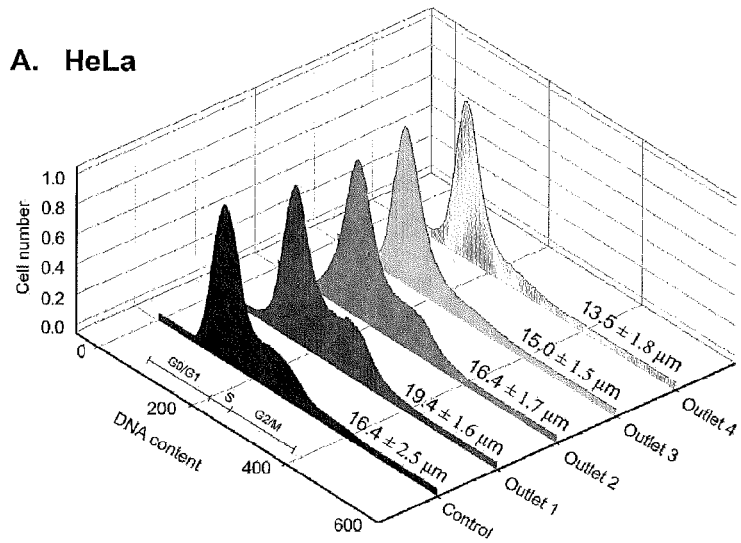
FIGS. 10A-10C are graphs showing cell cycle analysis results with permanent cell lines (10A=HeLa, 10B=KKU-100, 10C=CHO-CD36). The histograms indicate the distribution of the DNA content of the sorted singlet cells in the G0/G1, S and G2/M phase post synchronization. Cells in the G2/M phase have twice the amount of DNA than those in G0/G1 phase and hence double the fluorescence intensity. The larger cells collected from outlet 1 indicate an enrichment in the G2/M population ratio while the small cells collected from outlet 4 show significant enrichment of G0/G1 phase. The size distributions of the synchronized cells are also indicated on the plot.
Figure 10B:
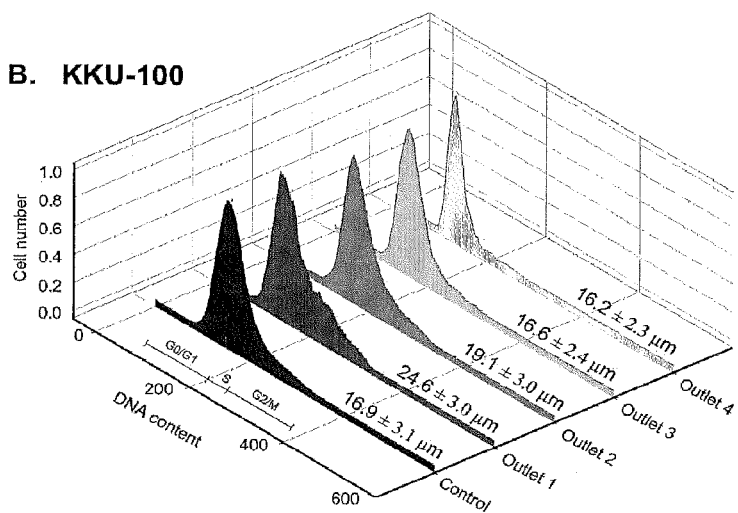
Figure 10C:
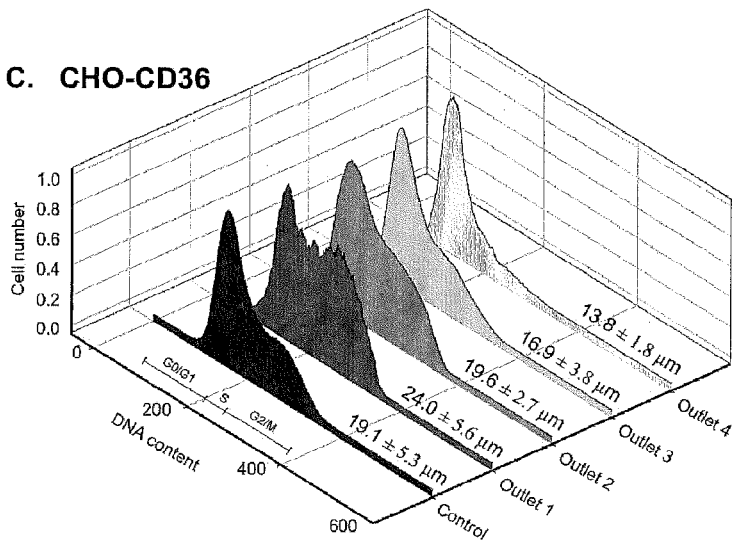

Cells in different phases of the cell cycle can be distinguished by the amount of cellular DNA content. The distributions of separated cells in the different phases were estimated using flow cytometric analysis. As mentioned earlier, cells in the G2/M phase have typically two times the DNA fluorescence intensity than cells in the G0/G1 phase. The percentage of cells in each phase was calculated and doublet and aggregate cells discriminated using fluorescent area and width plots (Wersto, R. P., et al., *Cytometry Part B: Clinical Cytometry*, 2001. 46(5): p. 296-306). FIGS. 10A-100C present histograms indicating the distribution of the DNA content of the sorted singlet cells in the G0/G1, S and G2/M phase after synchronization for the HeLa, KKU-100 and CHO-CD36 cells. Following separation, high synchrony of cells was achieved in cells collected from outlet 4 with 84% of HeLa, 96% of KKU-100 and 86% of CHO-CD36 cells synchronized to the G0/G1 phase. Concurrently, an enrichment of 2-3× in G2/M phase was achieved in cells collected from outlet 1.

These results are comparable with those reported using other microfluidic systems (Kim, U., et al., *Proceedings of the National Academy of Sciences*, 2007. 104(52): p. 20708; Thevoz, P., et al., *Analytical chemistry*, 2010. 82: p. 3094-3098; Choi, S., et al., *Analytical chemistry*, 2009. 81(5): p. 1964-1968; Migita, S., et al., *Analytical Methods*, 2010. 2: p. 657-660). However, the high flow throughput of this technique can fractionate ~15×10$^6$ cells/hr significantly higher than other reported microfluidics methods. The passive sorting principle also ensures >90% cell viability. A summary of the various microfluidic cell cycle synchronization systems are presented in Table 2.

TABLE 2

Distribution of the sorted hMSCs in the various cell cycle phase post synchronization.

| | | Distribution (%) | | | | |
|---|---|---|---|---|---|---|
| Cell Type | Phase | Control | Outlet 1 | Outlet 2 | Outlet 3 | Outlet 4 |
| HeLa | G0/G1 | 70.0 | 55.0 | 56.0 | 79.0 | 84.0 |
| | S | 11.0 | 15.0 | 18.0 | 11.0 | 9.0 |
| | G2/M | 19.0 | 30.0 | 26.0 | 10.0 | 7.0 |
| KKU-100 | G0/G1 | 74.2 | 67.7 | 64.8 | 81.1 | 96.4 |
| | S | 15.4 | 13.3 | 20.5 | 11.9 | 2.3 |
| | G2/M | 10.4 | 19.0 | 14.7 | 7.0 | 1.4 |
| CHO-CD36 | G0/G1 | 55.0 | 37.0 | 43.0 | 62.0 | 86.0 |
| | S | 16.0 | 17.0 | 19.0 | 14.0 | 8.0 |
| | G2/M | 29.0 | 46.0 | 38.0 | 24.0 | 6.0 |
| hMSCs | G0/G1 | 56.4 | 29.6 | 50.8 | 72.6 | 86.2 |
| | S | 16.6 | 19.8 | 17.8 | 12.0 | 5.9 |
| | G2/M | 27.0 | 50.6 | 31.4 | 15.4 | 7.9 |

Synchronization of primary culture- human Mesenchymal Stem Cells (hMSCs)

The ability of the device to synchronize a primary cell line-bone marrow derived human mesenchymal stem cells (hMSCs) was then tested. Unlike cancer cell lines or transformed cell lines, the hMSCs are highly susceptible to contact inhibition. Analysis on the cellular DNA content of hMSCs seeded at densities of 1500 cm$^{-2}$ and 3000 cm$^{-2}$ have substantially fewer cells in the S and G2/M phases after two days in culture. Thus, to enrich the S and G2/M population, cells were seeded at a lower density of 500 cm$^{-2}$ and cultured for two days before sorting. FIGS. 11A-11C present optical micrographs and viability results of the sorted hMSCs collected from outlets 1-4. The hMSCs collected from outlet 1 had a mean cell diameter of 23.5±5.6 µm and were significantly larger than those collected from outlet 4 (approximately 15.5±2.1 µm). Following separation, the

TABLE 1

Comparison of microfluidic separation techniques reported for cell cycle synchronization

| | | | | | Synchrony | | |
|---|---|---|---|---|---|---|---|
| Reference | Method | Separation Principle | Separation Type | Cell Lines | G0/G1 purity | G2/M enrichment | Throughput |
| Kim et al. | Dielectrophoresis | Inhomogeneous electric field | Active | MDA-MB-231 | 96% | | 2 × 10$^5$ cells/hr |
| Thevoz et al. | Acoustophoresis | Ultrasonic standing waves | Active | MDA-MB-231 | 84% | ~1×* | 3 × 10$^6$ cells/hr |
| Choi et al. | Hydrophoresis | Inhomogeneous pressure field | Passive | U937 | ~96% | 23×* | 2.4 × 10$^5$ cells/hr |
| Migita et al. | Hydrodynamic filtration | Hydrodynamic force | Passive | HepG2 | 86% | 3.7× | 3 × 10$^6$ cells/hr |
| | | | | NIH/3T3 | 81% | 2.9× | |
| This work | Inertial | Life forces and Dean drag | Passive | MSCs | 86% | 3.6× | 15 × 10$^6$ cells/hr |
| | | | | CHO-CD36 | 82% | 3.1× | |
| | | | | HeLa | 84% | 2× | |
| | | | | KKU-100 | 96% | 2× | |

*Estimated from data presented in the paper.

viability of the cells was assessed via trypan blue exclusion assay and through long-term re-culturing. The viability of the sorted cells was similar to that of the control unsorted MSCs with more than 90% of the cells collected from each outlet excluding the dye, indicating that the cells were sorted without incurring any physical damage (FIG. 11B). After 14 days of culture, the morphology of the sorted hMSCs was similar to that of the unsorted (control) cells, further demonstrating the maintenance of cell viability post sorting (FIG. 11C).

In the control MSC culture, 56.2% of the cells were found in G0/G1, 24.3% in S and 19.9% in the G2/M phase as shown by the DNA histogram (FIG. 12). Post synchronization, the cell population collected from outlet 2 had a combined 72.7% in the S and G2/M phases while 86.1% of the cells from outlet 4 were synchronized to the G0/G1 phase (Table 1). These results indicate that the G0/G1 to G2/M ratio of 3:1 of the asynchronous sample is enriched to 16:1 from the sample collected at outlet 4. Similarly, four-fold enrichment in the G2/M population is achieved from the sample collected at outlet 1.

To experimentally confirm that the hMSCs were synchronizing in the G0/G1 phase, the synchrony of the smallest hMSCs population (outlet 4) was compared with the hMSCs arrested in the G0/G1 phase by means of serum starvation and contact inhibition. It was found that 86.2% of the hMSCs collected from outlet 4 of the device were synchronized in the G0/G1 phase compared to 76.4% by contact inhibition and 77.5% by serum starvation for 48 h. The corresponding diameters of the hMSCs collected from outlet 4 (15.5±2.1) μm have a narrower size distribution than the serum starved (16.9±4.2 μm) and contact inhibited (23.3±3.8 μm) cells. It was noted that contact inhibition produced cells with a similar amount of DNA but the cell size of the arrested population was as heterogeneous as the original culture (21.9±13.5). While the main criterion for successful synchronization is that the DNA content in the synchronized cell population should be similar, the size distribution of the cells should also be relatively uniform as compared to the initial cells (Cooper, S., *Cellular and Molecular Life Sciences*, 2003. 60(6): p. 1099-1106). The wide variation in cell diameter of the contact inhibited group indicates that the cells were merely arrested with a similar amount of DNA but other cellular processes leading to protein and mass synthesis were not really synchronized. Conversely, withdrawal of serum from culture synchronized the hMSCs with G1 phase amount of DNA and arrested mass synthesis, but the size range of the cells was still relatively large as compared to those synchronized by our device. Therefore, the serum starved cells were not truly synchronized despite having relatively similar amount of DNA. It was also noted that the shape of serum starved hMSCs were more irregular with relatively more blebs indicating that the normal physiology of the hMSCs is disrupted under serum starvation-induced stress.

Figure 13:
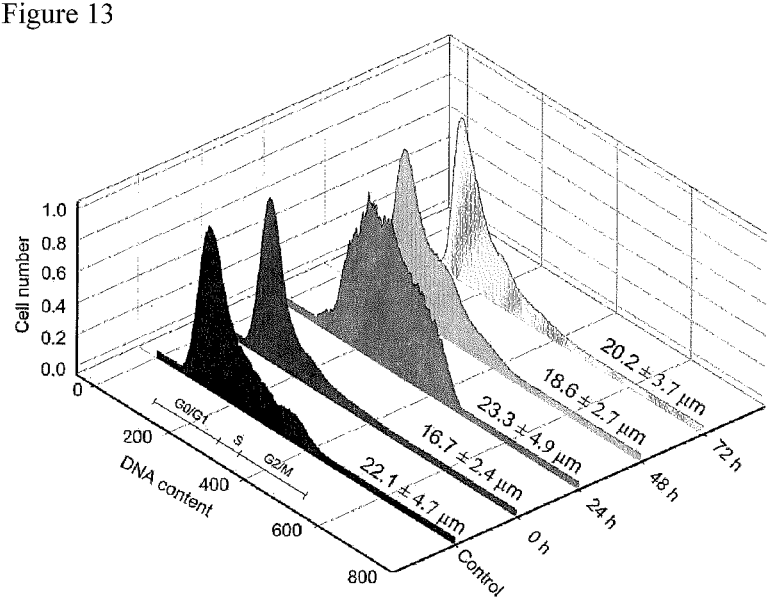
FIG. 13 shows histograms indicating the distribution of the DNA content of the sorted hMSCs collected from outlet 4 at different increasing time intervals. The hMSCs demonstrate synchronized cell division as all the outlet 4 hMSCs (82.3% at 24 h) transit to S and G2/M phase at day 1 (79.7%). The percentage of cells in G0/G1 increases from day 2 onwards due to contact inhibition. The synchrony decays over time due to stochastic variations in the interdivision times.

Whether the hMSCs synchronized by the device undergo synchronized divisions was next investigated. The underlying assumption is that synchronized cells do not merely have similar sizes and DNA content but the cells are capable of passing through the cell cycle as a relatively uniform cohort. To test this hypothesis, the hMSCs collected from outlet 4 with 86% of G0/G1 synchrony was replated and their DNA content analyzed 24, 48 and 72 h later (FIG. 13). Interestingly, after 24 h of culture, the percentage of cells in the S and G2/M was 79.7% indicating that most of the G0/G1 cells have progressed through the subsequent phases (Table 3).

TABLE 3

Distribution of the cell cycle phase of the replated hMSCs from outlet 4 at varying time points post synchronization Distribution (%)

| Phase | Control | 0 h | 24 h | 48 h | 72 h |
|---|---|---|---|---|---|
| G0/G1 | 64.5 | 82.3 | 19.7 | 51.9 | 69.4 |
| S | 23.2 | 14.3 | 45.2 | 34.7 | 23.9 |
| G2/M | 11.8 | 3.3 | 34.6 | 12.7 | 6.6 |

Typically, mammalian cells reside in the G1/S phase for 16-24 h and only about 2-3 h in G2/M phases (Kim, U., et al., Selection of mammalian cells based on their cell-cycle phase using dielectrophoresis. *Proceedings of the National Academy of Sciences*, 2007. 104(52): p. 20708). It is therefore expected that the majority of the cells were found in the S and G2/M phases 24 h after culture. However, the synchrony of the cells decayed over time as a result of stochastic variation in interdivision times. The population of G0/G1 hMSCs increased to 69.4% after 74 h of culture due to contact inhibition of cell growth. Many chemical methods or "batch treatments" such as aphidicolin, roscovitine and colchicine have been used to arrest cell cultures at a specific phase of the cell culture but the normal cellular progression is often disrupted (Choi, S., et al., *Analytical chemistry*, 2009. 81(5): p. 1964-1968). For example, Whitfield et al., employed thymidine-nocodazole block to arrest HeLa cells in the G2 phase (Whitfield, M. L., et al., *Molecular Biology of the Cell*, 2002. 13(6): p. 1977). Following release from the arrest procedures 12 h later, cells from all phases of the cell cycle were present rather than cells from only one or at most two phases. In contrast, the results herein show that hMSCs synchronized by the device exhibit relatively synchronized divisions.

Conclusions

Demonstrated herein is the application of spiral microfluidic device employing the combined effect of inertial forces and Dean drag force for fractionating mammalian cells into different stages of the cell cycle on the basis of size. The device offers many distinct advantages over other microfluidic separation methods including continuous operation enabling very high sample throughput (~15×10$^6$ cells/hr), thereby significantly reducing sample processing time. Passive operating principle eliminates the need to integrate external force fields for functionality or inhibitory chemicals, thereby preserving the integrity and viability of sorted cells (>90%). Thus, demonstrated herein is that use of microfluidics offers high throughputs for cell cycle synchronization with significantly higher viability. As mammalian cell suspension can be separated and synchronized directly, sample preparatory steps are not necessary unlike other methods such as the FACS and CCE, further reducing processing time and cost. The high throughput and minimally invasive nature of the cell cycle microfluidic device could find diverse applications in biotechnological research and utility.

Example 3

Shear Modulated Abstraction of Rare-Cells Technology Biochip for High Throughput Isolation of Circulating Tumor Cells Materials and Methods Cell Culture and Sample Preparation Two human breast adenocarcinoma cell lines, MCF-7 and MDA-MB-231, were tested in this work. The MCF-7 cells (HTB-22™, ATCC, USA) and MDA-MB-231 cells (HTB-26™, ATCC, USA) were cultured in low-glucose Dulbecco's modified Eagle's medium (DMEM) (Invitrogen, USA) supplemented with 10% fetal bovine serum (FBS) (Invitrogen, USA) together with 1% penicillin-streptomycin (Invitrogen, USA). The culture was maintained at 37° C. in a humidified atmosphere containing 5% (v/v) $CO_2$. The cells were cultured in sterile 25 $cm^2$ flasks (Corning) and subcultivated (1:4) three times a week with media replaced every 48 h. Sub-confluent monolayers were dissociated using 0.01% trypsin and 5.3 mM EDTA solution (Lonza, Switzerland). For the control and recovery experiments, the cancer cells were diluted in buffer containing 1× phosphate buffered saline (PBS), 2 mM ethylenediaminetetraacetic acid (EDTA) supplemented with 0.5% bovine serum albumin (BSA) (Miltenyi Biotec, Germany) to prevent non-specific adsorption to the tubing and microchannel walls. The buffer density was increased by supplementing with 3% w/v Dextran 40 (AppliChem Asia, Singapore) to prevent cell sedimentation (Hou, H. W., et al., *Lab on a chip,* 2010. 10(19): p. 2605-2613). For RBC equilibration experiments, whole blood obtained from healthy donors was spun down to separate the RBCs. Final sample concentration was adjusted to varying hematocrit (0.5%-5%) with sample buffer accordingly. For leukocyte control experiments, whole blood was treated with RBC lysis buffer (eBioscience, USA) according to the manufacturer's instructions to obtain a pure population of leukocytes.

Microchannel Fabrication

The devices were fabricated in polydimethylsiloxane polymer (PDMS, Sylgard 184, Dow Corning, USA) using a double molding process (Hou, H. W., et al., *Lab on a chip,* 2010. 10(19): p. 2605-2613). The contraction-expansion microchannels were first patterned on silicon wafers using AZ®P4620 photoresist. Following lithography, the microchannels were etched into silicon using deep reactive ion etching (DRIE). Next the photoresist was stripped and the patterned silicon wafers were silanized with trichloro (1H, 1H, 2H, 2H-perfluorooctyl) silane (Sigma Aldrich, USA) for 2 h to facilitate PDMS mold release. PDMS prepolymer mixed in 5:1 (w/w) ratio with curing agent was then poured on the silicon wafer and cured at 70° C. for 2 h. Higher ratio of curing agent was used to promote increased cross-linking, thus making the PDMS molds more rigid for fabrication of high aspect ratio structures which are easily prone to deformation. This cured PDMS mold now acts as a master for subsequent PDMS casting (negative replica). The PDMS master template was then silanized for 2 h to promote release of subsequent PDMS molds with patterned microchannels. Finally, holes for inlet and outlets were punched and the PDMS molds were then irreversibly bonded to microscopic glass slides by briefly exposing to an oxygen plasma environment (Covance, Femto Science, South Korea). Following plasma treatment, the surfaces were immediately brought into contact with each other and allowed to stay for 3 h at 70° C. to complete the bonding.

Device Characterization

During testing, the sample was pumped into the microfluidics devices at varying Reynolds number (Re) using a syringe pump (NE-1000, New Era Pump Systems Inc., USA). The microchannels were mounted on an inverted phase contrast microscope (Olympus IX71) equipped with a high speed CCD camera (FASTCAM 1024 PCI, Photron, USA). High speed videos captured at the channel outlet were then analyzed using ImageJ® software.

Immunofluorescence Staining and FACS Analysis

Results from experiments conducted to determine the collection efficiency, recovery and enrichment ratio were analyzed by performing flow cytometry analysis using BDTM LSR II flow cytometer (BD Biosciences, USA) on the centre and side outlet samples. Immunofluorescence staining allowed differentiating the various cell types for visualization and quantification. The outlet samples were incubated with FcR blocking reagent (1:100, Miltenyi Biotec Asia Pacific, Singapore) for 15 min to block out non-specific bindings followed by incubation with allophycocyanin (APC) conjugated Epithelial Cell Adhesion Molecule (EpCAM) (1:100, Miltenyi Biotec Asia Pacific, Singapore) for 40 min to identify the cancer cells. The peripheral blood leukocytes were identified by staining with fluorescein isothiocyanate (FITC) conjugated CD45 (1:100, Miltenyi Biotec Asia Pacific, Singapore) marker for 40 min.

Results and Discussion

As RBCs make up for >99% of all hematologic cells, complete removal of RBCs is pivotal for achieving meaningful enrichment. The microchannel design and testing conditions were optimized by studying the effect of various parameters including microchannel aspect ratio, flow rate and sample hematocrit on RBC focusing and removal from the side outlets.

Effect of Aspect Ratio (AR)

Figure 17A:
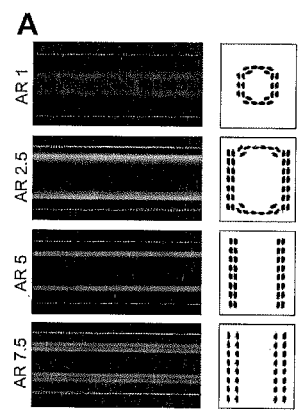
FIGS. 17A and 17B show the effect of microchannel aspect ratio (AR) on red blood cell focusing. 17A Averaged composite images illustrating RBC equilibration for increasing aspect ratios. The input blood sample was fixed at 1% hematocrit pumped at Re=100. The microchannels begin with a 200 µm wide segment at the input and at the output opened into a 300 µm wide section immediately prior to the bifurcation for enhanced separation. Adjacent schematics indicate the approximate position of the RBCs within the microchannel cross-section at the outlet (dotted lines indicate approximate position of channel walls). 17B Linescans representing the probability distribution of RBCs across the microchannel width measured at the outlet. The outlet distribution indicating the position of the side outlets is also indicated on the plot.
Figure 17B:
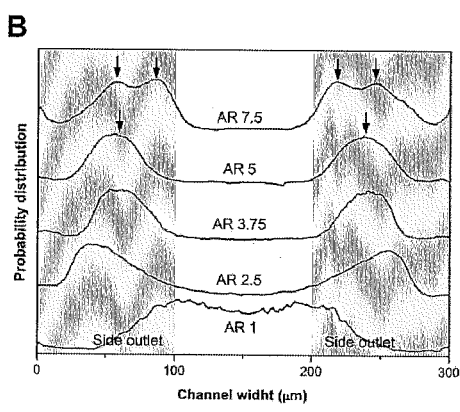

FIGS. 17A and 17B present the effect of microchannel aspect ratio on RBC focusing. In microchannels with rectangular cross-sections, the shear-modulation across the channel cross-section can be exploited to preferentially equilibrate cells along the longer channel dimension. Another advantage of high aspect ratio is the ability to process the sample at higher flow rate, thereby increasing the throughput. To study the effect of aspect ratio, microchannels of height 20 µm, 50 µm, 75 µm, 100 µm and 150 µm were fabricated yielding aspect ratios of 1, 2.5, 3.75, 5, and 7.5 respectively. Composite images and linescans indicating the RBC distribution across the channel as a function of aspect ratio are presented in FIGS. 17A and 17B.

In square microchannels (AR 1), at Re=100 and 1% hematocrit the RBCs equilibrates in an annular fashion forming a weakly focused cellular ring across the channel cross-section (as depicted in the schematic). The uniform fluidic shear across the cross-section requires longer microchannel lengths for the cells to strongly focus in their equilibrium positions. Increasing the aspect ratio to 2.5 initiates the preferential migration of cells across the channel width and equilibration along the microchannel height. However, the linescans clearly indicates that not all RBCs have focused in the equilibrium positions in the given channel length. In microchannels with aspect ratio 3.75, all RBCs equilibrate at the microchannel height. This is evident by the formation of a prominent cell-free region along the microchannel center. Further increasing the aspect ratio to 5 causes the migration of the two strongly focused cellular band closer towards the channel sidewalls. An interesting effect is seen when we increase the microchannel aspect ratio to 7.5. In this very high aspect ratio channel, the breaking-up of the focused RBC bands into two, an inner and outer band is observed. This observation is in accordance with very recent experimental and modeling work studying the effect of aspect ratio on inertial migration (Bhagat, A. A. S., Shear-modulated inertial migration 2009, University of Cincinnati: Cincinnati; Gupta, A, et al., in 47*th AIAA Aerospace Sciences Meeting.* 2009. Orlando). The exact mechanisms responsible for this behavior are still unclear and warrant further investigation. However, this effect is unfavorable for separation applications and thus we limit this work to channels with maximum aspect ratio 5.

Effect of Reynolds Number (Re) FIGS. 18A-18C present the effect of Re on RBC focusing. For high throughput it is necessary to process the blood sample at high flowrates. Tests were conducted using 1% hematocrit sample in AR 5 (h=100 µm) microchannel. The RBC equilibration was studied for Re ranging from 10 to 150. Higher flowrates could not be tested due to the high pressure drops across the microchannels resulting in device failure. At low flowrates (Re≤25) the inertial lift forces acting on the RBCs are weaker than the viscous drag force, thus no equilibration is observed. Increasing the flow rate to Re=50 and above enables the RBCs to overcome the drag forces and migrate preferentially towards the channels side walls, forming two well-defined cellular-bands (observed as two distinct peaks when imaging from either the top or the bottom). It was also observed that the migration of the RBCs equilibrium positions closer to the microchannel walls with increasing Re (Chun, B. et al., *Physics of Fluids*, 2006. 18: p. 031704).

To quantify the degree of focusing as a function of Re, two parameters were defined: cell-free region width and the cell-band width (FIG. 18B). The cell-free region width is the normalized microchannel width at the microchannel center which is completely devoid of any RBCs. It is calculated from the RBCs probability distribution profile by measuring the full width at half maximum (FWHM) of the distance between the two cell occupied regions. Similarly, the cell-band width is calculated by measuring the FWHM of the region occupied by the RBCs. FIG. 18C plots the cell-free region and the cell-band width as a function of Re. As Re increases, the large inertial lift forces induce stronger RBC focusing; evident with a decrease in the cell-band width (FIG. 18C). Consequently, the width of the cell-free region increases with increasing flowrate. At low Re (<100), the reduction in the cellband width, as a result of tighter RBC focusing, accounts for the increase in the cell-free region at the microchannel center. Beyond Re=100, although the width of the cell-band remains constant, the increase in the cell-free region is accounted by the migration of the two RBC-bands closer to the channel sidewalls. For optimal RBC focusing and collection at the side outlets, it is important to operate in the strongly focused region (≥100) of the Re range (FIG. 18C).

Effect of Hematocrit

Next the highest sample hematocrit that can be processed in these microchannels without significant loss in RBC focusing was determined. For applications involving whole blood processing (~40% hematocrit), it is desirable to work with high hematocrit to reduce processing and analysis time. The cell-free region and the cell-band width parameters were used to determine the optimal test conditions. Experiments were conducted with hematocrit ranging from 0.5% to 5% at Re=100 in an AR 5 microchannel. Composite images and linescans presenting the effect of increasing hematocrit on RBC equilibration are shown in FIGS. 19A-19C. As the input hematocrit was increased, the width of the RBC band increased in a linear fashion consequently decreasing the width of the central cell-free region. This trend is expected for increasing volume fraction (hematocrit) as more RBCs try to occupy the equilibration positions resulting in significant cell-cell interaction induced dispersion.

An interesting effect was observed when the hematocrit was increased to 3% and above. As seen earlier in microchannels with aspect ratio 7.5, the breaking up of the cell-band into two prominent inner and outer bands was again observed. While the formation of these multiple bands had been observed earlier in high aspect ratio microchannels (Gupta, A, et al., in *47th AIAA Aerospace Sciences Meeting*. 2009. Orlando), this indicates the role of volume fraction on initiating this phenomenon. Again, the formation of these inner and outer bands is unfavorable for separation applications, as it reduces the width of the central cell-free region. For this reason, this work is limited to samples with maximum hematocrit of 2%, implying a 20× whole blood dilution prior to testing.

Effect of Pinching Width on CTC Isolation and Recovery

Figure 20:
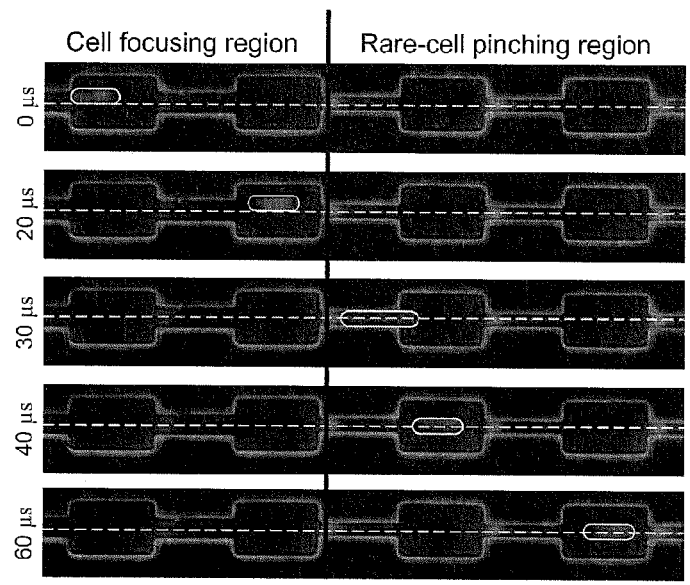
FIG. 20 is an illustration of time-sequential images indicating the rare-cell isolation principle of the developed microfluidic device. In the cell-focusing region the CTCs (MCF-7 cells marked by yellow circles) under the influence of shear-modulated inertial forces equilibrate along the microchannel sidewalls. This is evident in the expansion region of the channel as the CTCs remain displaced to either side of the microchannel center (white dotted line indicates the approximate channel center). Passing through the pinched section, the center of inertia of CTCs align with the center of the microchannel width. In the expansion region the CTCs continue to follow the flow streamlines and stay aligned along the center of the microchannel width.

As mentioned in the design principles section, the 'pinching' width is used for the successful isolation of rare-cells from other hematologic cells. The contraction width along this pinching region is designed to be comparable to (smaller, or on the order of) the rare-cell diameter, ensuring that the rare cells are effectively 'squashed' as they traverse through the contraction channels. Thus, the center of inertia of these larger cells is aligned along the axial centre of the microchannel during discharge into the expansion region, achieving separation (Yamada, M., et al., *Anal. Chem.*, 2004. 76(18): p. 5465-5471) (FIG. 20). As a demonstration, this technique was used for the isolation of CTCs.

Figure 21A:
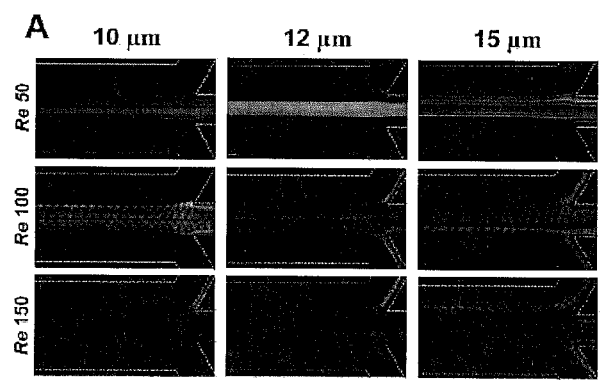
FIGS. 21A and 21B show the effect of channel width in the cell-pinching region on CTC separation efficiency. 21A Averaged composite images illustrating MCF-7 cells isolation in the center outlet for increasing flowrate in microchannels with varying "pinching" widths (dotted lines indicate approximate position of channel walls). 21B Plot indicating the fraction of MCF-7 cells and peripheral blood leukocytes collected at the center outlet for increasing Re.
Figure 21B:
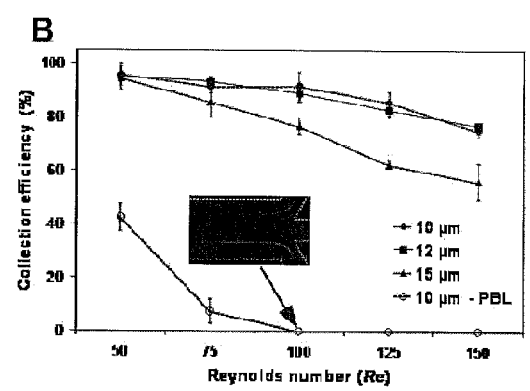

Two human breast adenocarcinoma cell lines, MCF-7 and MDA-MB-231, with average measured diameters of 18.1±1.8 µm and 18.2±2.8 µm respectively were tested. As the average size of the CTCs is larger than 15 µm (Tan, S., et al., *Biomedical Microdevices*, 2009. 11(4): p. 883-892; Von a, G., et al., *American Journal of Pathology*, 2000. 156(1): p. 57-63), microchannels with 10 µm, 12 µm and 15 µm pinching widths were designed to ensure minimum loss of CTCs at the side outlets. FIGS. 21A and 21B present the effect of pinching width on MCF-7 cells separation for increasing channel Re. At low Re=50, ~95% of tumor cells were collected at the centre outlet for all three contraction widths. Increasing the Re resulted in a decrease in the collection efficiency, possibly due to the large deformability of cancer cells under high laminar shear stresses (Lincoln, B., et al., *Cytometry Part A*, 2004. 59(2): p. 203-209; Hou, H. W., et al., *Biomedical microdevices*, 2009. 11(3): p. 557-564). At high flow rates, the surface tension mismatch between the suspended cells and carrier buffer induced interfacial stresses leading to CTCs shape distortion. The viscoelastic cell deforms from a spherical shape to an elongated prolate spheroid (Born, C., et al., *Biotechnology and Bioengineering*, 1992. 40(9): p. 1004-1010). As the CTCs are elongated, their critical dimensions become smaller than the initial diameter, thus precluding them from being pinched effectively. Pressure induced PDMS deformation at high flowrates, an important but often overlooked factor, could also be partly responsible for the decrease in collection efficiency at high flow rates. Considering alternate materials such as hard plastics (PMMA, COC) would likely overcome this issue, thereby increasing the collection efficiency. As the CTCs are an extremely rare population, a collection efficiency cut-off of 90% was targeted in this work. Results from experiments conducted with only RBCs suggest Re=100 flows are optimal for their removal from the side outlets. Based on these results, the 10 µm channel width was selected for efficient CTC collection. Similar results were observed for the MDA-MB-231 cells.

The cancer cells passing through the pinching region undergo considerable deformation and their integrity and viability is thus of concern due to the large stress and high shear experienced by them. Following separation, the cell viability was tested by reseeding the MCF-7 cells back into culture using the procedure described in the methods section to observe their proliferation and growth. After 4 days of culture, the proliferation rate of the isolated MCF-7 cells was similar to that of the control cells with no noticeable change in the morphology. The result confirms that the developed technique has minimal effect on the cells during isolation maintaining high cell viability post sorting.

For subsequent downstream CTC analysis, it is important to minimize contamination due to the presence of peripheral blood leukocytes (PBL) in the isolated samples. To assess the device efficiency for PBL removal, a pure population of human leukocytes isolated by RBC lysis was run through the microchannel (pinching width=10 µm) at varying Re. As the mean diameter of human leukocytes is smaller than 10 µm in diameter (Sethu, P., et al., *Lab on a Chip*, 2006. 6(1): p. 83-89; Schmid-Schonbein, G. W., et al., *Blood*, 1980. 56(5): p. 866; Downey, G. P., et al., *Journal of Applied Physiology*, 1990. 69(5): p. 1767), the flow path of the PBL in the cell pinching region remained unchanged and are thus filtered out from the side outlets (FIG. 21B). As evident from the figure, at Re 50 and 75 a fraction of PBL are still collected at the center outlet due to weak inertial cell focusing. However at Re≥100, all the leukocytes equilibrated along the channel sidewalls with no cells collected at the center outlet (collection efficiency ~0%).

To further evaluate the device performance, varying concentrations of MCF-7 cells were spiked into PBS buffer and recovered from the center outlet of the biochip. The inlet and center outlet samples were analyzed using FACS to ascertain the recovery rate. CTC loss during testing could lead to potentially erroneous diagnosis. The results indicate a 90% recovery rate consistent with the CTC isolation efficiency, implying negligible cell loss during sample collection and analysis. A decrease in CTCs recovery (to ~85%) was observed at higher concentration ($10^4$ cells/mL) possibly due to increased interactions between cells along the pinching region.

CTC Enrichment in Blood

Following the characterization of device dimensions and operating conditions, MCF-7 cells spiked into whole blood were analyzed in the device using the optimal parameters. The MCF-7 cells (500 cells/mL) spiked blood sample was diluted to ~1.5-2% hematocrit and pumped through aspect ratio=5 microchannels at Re=100. The width of the cell pinching region was fixed at 10 µm. Outlet samples labeled with fluorescent markers were analyzed using FACS and hemocytometer to calculate the separation enrichment. The results are tabulated in Table 4 and indicate ~300× enrichment over RBC and ~850× enrichment over PBL with ~85% CTC recovery in a single pass through the SMART device ($1^{st}$ stage).

TABLE 4

Experimental data of the relative concentrations of RBCs, leukocytes and MCF-7 cells recovered from the center outlet of the device measured by FACS and hemocytometer counting.

| Sample | Concentration (%) | | |
|---|---|---|---|
| | RBCs 100 | Leukocytes 100 | MCF-7 100 |
| $1^{st}$ stage | 0.304 ± 0.003 | 0.115 ± 0.013 | 84.51 ± 2.85 |
| $2^{nd}$ stage | 3.10E−04 ± 3.76E−05 | 0.008 ± 0.007 | 81.10 ± 4.13 |

Although these enrichment ratios are appreciable for most cell separation applications, separations involving blood cells ideally require $10^7$-$10^8$ enrichment (Lara, O., et al., *Experimental hematology*, 2004. 32(10): p. 891-904). The enrichment ratio in this work was limited as the presence of the large CTCs in the pinching region disturbed the flow field in its immediate vicinity. As a result, a small fraction of RBCs and PBL were collected at the center outlet. This is evident from the high speed videos captured at the outlet where the arrival of CTCs is always accompanied with bursts of unfocused blood cells. Thus, to achieve higher and meaningful enrichments for CTC detection, samples collected from the center outlet of the device were processed again through the device to completely eliminate the contaminating hematologic cells ($2^{nd}$ stage). This was implemented by connecting the outlet tubing from the $1^{st}$ stage to another device in a cascaded configuration. By adding a $2^{nd}$ stage, the MCF-7 enrichment increases significantly to $3.25\times10^5$ (5.5 $\log_{10}$) fold over RBCs and ~$1.2\times10^4$ (4.1 $\log_{10}$) over PBL, with minimal loss in overall CTC recovery (~81%). This converts to approximately 15,000 RBCs and less than 850 PBL per mL of blood (assuming 5 billion RBCs and million PBL in one mL of whole blood).

The enrichment performance of the device is comparable to other popular CTC sorting techniques (Nagrath, S., et al., *Nature*, 2007. 450(7173): p. 1235-1239; Tan, S., et al., *Biomedical Microdevices*, 2009. 11(4): p. 883-892; Mohamed, H., et al., *Journal of Chromatography A*, 2009. 1216(47): p. 8289-8295; Vona, G., et al., *American Journal of Pathology*, 2000. 156(1): p. 57-63; Zheng, S., et al., *Journal of Chromatography A*, 2007. 1162(2): p. 154-161; Zabaglo, L., et al., *Cytometry Part A*, 2003. 55(2): p. 102-108; Lara, O., et al., *Experimental hematology*, 2004. 32(10): p. 891-904). For example, the polycarbonate membrane filtration method employed by Zabaglo et al., report >90% CTC recovery with 0.1% PBL (Zabaglo, L., et al., *Cytometry Part A*, 2003. 55(2): p. 102-108). The ISET technique reported by Vona et al., reports superior CTC enrichment with ~80% recovery and only 20 PBL per mL of blood (Vona, G., et al., *American Journal of Pathology*, 2000. 156(1): p. 57-63). Lara et al., reported a 5.17 $\log_{10}$ fold CTC enrichment using a two step negative selection technique combining red blood cell lysis with immunomagnetic PBL depletion (Lara, O., et al., *Experimental hematology*, 2004. 32(10): p. 891-904). The enrichment factor is comparable to the device as 100% of RBCs were efficiently depleted by lysis while the isolated samples remain contaminated with DNA from approximately 0.3% PBL. The performance of the device is also comparable to immunomediated (including immunomagnetic, immunofluorescent and immunobinding) CTC separation methods capable of achieving $10^4$-$10^6$ fold enrichment (Nagrath, S., et al., *Nature*, 2007. 450(7173): p. 1235-1239; Paterlini-Brechot, P. and N. L. Benali, *Cancer letters*, 2007. 253(2): p. 180-204).

The versatility of the device for isolating other low abundance cells from blood was demonstrated by successfully enriching leukocytes from RBCs. This was achieved by simply varying the contraction width in the cell pinching region to 8 µm allowing the collection of larger PBL at the center outlet (PBL size varies from 6-10 µm (Sethu, P., A. Sin, et al., *Lab on a Chip*, 2006. 6(1): p. 83-89; Schmid-Schonbein, G. W., et al., *Blood*, 1980. 56(5): p. 866; Downey, G. P., et al., *Journal of Applied Physiology*, 1990. 69(5): p. 1767). By efficiently removing all the RBCs through the side outlet, the device achieves a 100 fold leukocyte enrichment at the center outlet with ~60% PBL recovery.

For on-chip blood analysis and rare-cell isolation from blood, high throughput is important to process milliliters of clinical blood samples within a short period of time. By testing a 2% hematocrit sample at 400 µl/min flowrate (Re 100), the device is capable of processing ~$10^8$ cells/min using a single device. This translates to ~50 min of process time for 1 mL whole blood. Designing just four parallel channels, the analysis time can be practically reduced to less than 15 min/mL of blood, significantly faster than other popular CTC detection techniques. Microfluidics immunobinding methods are typically limited to low flow rate processing to allow maximum interaction between the CTCs and antibodies-coated surfaces, and to prevent CTCs detachment during separation (Nagrath, S., et al., *Nature,* 2007. 450(7173): p. 1235-1239; Gleghorn, J. P., et al., *Lab on a Chip,* 2010. 10(1): p. 27-29). Common microfluidic filtration methods associated with physical entrapment of CTCs are also limited to low flow rates to ensure the CTCs remain trapped without deforming through the traps or pores (Adams, A. A., et al., *Journal of the American Chemical Society,* 2008. 130(27): p. 8633-8641; Tan, S., et al., *Biomedical Microdevices,* 2009. 11(4): p. 883-892). Moreover, trapping efficiency decreases at higher CTCs count as the physical presence of any trapped CTCs alters the flow pattern within the trapping region. Additional washing steps required after blood processing along with complicated retrieval procedures for analysis further increase the total processing time. The device offers continuous sorting and collection capability allowing retrieval of CTCs for downstream molecular assays such as gene analysis, drug screening and molecular-targeted cancer therapy. The isolated cells can also be enumerated and analyzed in real-time rather than performing an end-point investigation.

Conclusions

A high throughput and highly sensitive technique to isolate viable rare-cells from blood was described. Shear-modulated inertial cell focusing was employed in the device to achieve size-based isolation of low abundance cells from blood. As an application of the developed device, separation of CTCs from peripheral blood with high efficiency (~80%) and throughput (~400 µL/min) was demonstrated. The device offers $3.25 \times 10^5$ fold enrichment over red blood cells (RBCs) and $1.2 \times 10^4$ enrichment over PBL using a 2-stage cascaded arrangement. Although sample dilution is required, the simple channel design allows for easy parallelization with the ability to analyze milliliters of clinical blood samples within minutes. Integrating chip-based detection downstream the device will provide a competent tool for clinical cancer diagnosis. Finally, by customizing the pinching width for specific applications, the chip can be readily used for enriching other rare-cells from blood, including fetal and stem cells.

The relevant teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method of isolating one or more circulating tumor cells comprising:
   introducing a sample into a microfluidic device, the sample comprising a whole blood sample or a maternal whole blood sample, wherein the whole blood sample or the maternal whole blood sample comprises one or more circulating tumor cells to be isolated and smaller blood cells, the microfluidic device comprising a channel having a length, $L_c$, and a cross-section of a height in the range of between about 10 µm and about 200 µm and a width in the range of between about 100 µm and about 500 µm defining an aspect ratio adapted to isolate circulating cells along portions of the cross-section of the channel based on cell size,
   the channel comprising one or more spiral channels and having a hydraulic diameter, h, such that a cell diameter, $a_c$, of the circulating tumor cells to be isolated satisfies the ratio: $a_c/h \sim 0.1$, whereas the smaller blood cells have a smaller cell diameter than $a_c$ such that the ratio $a_c/h \sim 0.1$ is not satisfied for those cells,
   introducing a sheath fluid into the microfluidic device,
   flowing the sample through the channel at an average flow velocity, $U_f$, that causes the smaller blood cells to have undergone a transverse one-half Dean cycle migration across the channel at an outlet end of the channel such that the relation $$L_C = \frac{U_f}{U_{Dean}} \times L_{DC} \times \frac{1}{2}$$

is satisfied, where $L_c$ is the length of the channel, $U_f$ is the average flow velocity, $U_{Dean}$ is Dean velocity and $L_{DC}$ is a length for a complete Dean cycle migration around the channel, and
detecting and isolating the one or more circulating tumor cells from the sample,
wherein the introducing the sample and the introducing the sheath fluid comprises simultaneously introducing the sample and the sheath fluid into the microfluidic device via a radially innermost inlet and a radially outermost inlet, respectively, to confine the sample to a radially innermost portion of the channel at the inlet, and
wherein the detecting and isolating comprises the one or more circulating tumor cells flowing along a radially innermost portion of the channel to a first outlet and the smaller blood cells in the sample flowing along a radially outermost portion of the channel to a second outlet.

2. The method of claim 1, further comprising collecting circulating tumor cells from the first outlet.

3. The method of claim 2, further comprising analyzing the circulating tumor cells.

4. The method of claim 3, wherein analyzing the circulating tumor cells includes assessing effectiveness of a therapeutic treatment.

5. The method of claim 1, wherein the width of the channel at the end distal from the inlet is on the order of the cells to be isolated.

6. The method of claim 1, wherein the microfluidic device further includes at least one cell focusing region having a cross section adapted to cause all cells to migrate to and move along the longer channel dimension.

7. The method of claim 1, wherein the flowrate within the microfluidic device ranges from a Reynolds number of 10 to 150.

* * * * *